(12) United States Patent
Raksi et al.

(10) Patent No.: US 9,044,304 B2
(45) Date of Patent: Jun. 2, 2015

(54) PATIENT INTERFACE WITH VARIABLE APPLANATION

(75) Inventors: Ferenc Raksi, Mission Viejo, CA (US); Ilya Goldshleger, Irvine, CA (US)

(73) Assignee: Alcon LenSx, Inc., Aliso Viejo, CA (US)

( * ) Notice: Subject to any disclaimer, the term of this patent is extended or adjusted under 35 U.S.C. 154(b) by 376 days.

(21) Appl. No.: 13/336,324

(22) Filed: Dec. 23, 2011

(65) Prior Publication Data

US 2013/0165911 A1 Jun. 27, 2013

(51) Int. Cl.
*A61N 5/06* (2006.01)
*A61F 9/009* (2006.01)

(52) U.S. Cl.
CPC ..................................... *A61F 9/009* (2013.01)

(58) Field of Classification Search
CPC .................... A61B 2009/00897; A61B 9/008; A61B 2009/00872
USPC ........................................................ 606/1
See application file for complete search history.

(56) References Cited

U.S. PATENT DOCUMENTS

| | | |
|---|---|---|
| 3,706,304 A | 12/1972 | Sisler |
| 4,367,018 A | 1/1983 | Abe |
| 4,453,546 A | 6/1984 | Katz et al. |
| 4,600,008 A | 7/1986 | Schmidt |
| 4,718,418 A | 1/1988 | L'Esperance, Jr. |
| 4,753,526 A | 6/1988 | Koester |
| 4,905,711 A | 3/1990 | Bennett et al. |
| 4,907,586 A | 3/1990 | Bille et al. |
| 4,964,717 A | 10/1990 | Koester |
| 4,994,058 A | 2/1991 | Raven et al. |
| 5,108,412 A | 4/1992 | Krumeich et al. |
| 5,112,328 A | 5/1992 | Taboada et al. |
| 5,128,509 A | 7/1992 | Black et al. |
| 5,196,027 A | 3/1993 | Thompson et al. |
| 5,226,903 A | 7/1993 | Mizuno |
| 5,252,998 A | 10/1993 | Reis et al. |
| 5,280,491 A | 1/1994 | Lai |
| 5,311,224 A | 5/1994 | Enomoto |

(Continued)

FOREIGN PATENT DOCUMENTS

| | | |
|---|---|---|
| CA | 2128104 A1 | 7/1993 |
| EP | 0627207 | 12/1994 |

(Continued)

OTHER PUBLICATIONS

European Supplementary Search Report for European Application No. 08799433.1 with mailing date Feb. 13, 2013, 6 pages.

(Continued)

*Primary Examiner* — Aaron Roane

(57) ABSTRACT

A variable-applanation patient interface can include a lens support system, attachable to a distal end of an ophthalmic surgical laser system; a contact lens, supported by the lens support system and configured to make contact with an eye-surface; and an adjustable coupler, coupled to at least one of the lens support system and the contact lens, and configured to be coupled to a non-central region of the eye-surface, to accommodate the contact lens to contact a central region of the eye-surface with a central applanation, to enable a change between the central applanation and an extended applanation, and to accommodate the contact lens to contact an extended region of the eye-surface larger than the central region with the extended applanation.

19 Claims, 19 Drawing Sheets

(56) References Cited

U.S. PATENT DOCUMENTS

| | | | |
|---|---|---|---|
| 5,324,281 A | 6/1994 | Muller | |
| 5,336,215 A | 8/1994 | Hsueh et al. | |
| 5,360,424 A | 11/1994 | Klopotek | |
| 5,364,390 A | 11/1994 | Taboada et al. | |
| 5,423,801 A | 6/1995 | Marshall et al. | |
| 5,450,144 A | 9/1995 | Ben Nun | |
| 5,549,632 A | 8/1996 | Lai | |
| 5,656,186 A | 8/1997 | Mourou et al. | |
| 5,861,955 A | 1/1999 | Gordon | |
| 5,871,772 A | 2/1999 | Cantoro | |
| 5,957,832 A | 9/1999 | Taylor et al. | |
| 6,019,472 A | 2/2000 | Koester et al. | |
| 6,090,100 A | 7/2000 | Hohla | |
| 6,143,010 A | 11/2000 | Silvestrini et al. | |
| 6,210,401 B1 | 4/2001 | Lai | |
| 6,254,595 B1 | 7/2001 | Juhasz et al. | |
| 6,342,053 B1 | 1/2002 | Berry | |
| 6,344,040 B1 | 2/2002 | Juhasz et al. | |
| 6,373,571 B1 | 4/2002 | Juhasz et al. | |
| 6,412,334 B1 | 7/2002 | Kral et al. | |
| 6,436,113 B1 | 8/2002 | Burba et al. | |
| 6,451,006 B1 | 9/2002 | Bille | |
| 6,458,141 B1 | 10/2002 | Peyman | |
| 6,579,282 B2 | 6/2003 | Bille et al. | |
| 6,623,476 B2 | 9/2003 | Juhasz et al. | |
| 6,634,753 B1 | 10/2003 | Rozenman | |
| 6,641,577 B2 | 11/2003 | Bille | |
| 6,676,653 B2* | 1/2004 | Juhasz et al. | 606/4 |
| 6,730,073 B2 | 5/2004 | Bruce | |
| 6,730,074 B2 | 5/2004 | Bille et al. | |
| 6,733,491 B2 | 5/2004 | Kadziauskas et al. | |
| 6,752,778 B1 | 6/2004 | Fiedler et al. | |
| 6,776,824 B2 | 8/2004 | Wen | |
| 6,780,176 B2 | 8/2004 | Hasegawa | |
| 6,863,667 B2 | 3/2005 | Webb et al. | |
| 6,899,707 B2 | 5/2005 | Scholler et al. | |
| 6,905,641 B2 | 6/2005 | Platt et al. | |
| 6,991,629 B1 | 1/2006 | Juhasz et al. | |
| 7,018,376 B2 | 3/2006 | Webb et al. | |
| 7,125,119 B2 | 10/2006 | Farberov | |
| 7,238,176 B2 | 7/2007 | Loesel et al. | |
| 7,244,026 B1 | 7/2007 | Ross, III et al. | |
| 7,285,096 B2 | 10/2007 | Burba et al. | |
| 7,330,275 B2 | 2/2008 | Raksi | |
| 7,371,230 B2 | 5/2008 | Webb et al. | |
| 7,390,089 B2 | 6/2008 | Loesel et al. | |
| 7,402,159 B2 | 7/2008 | Loesel et al. | |
| 7,452,080 B2 | 11/2008 | Wiltberger et al. | |
| 7,452,081 B2 | 11/2008 | Wiltberger et al. | |
| 7,611,507 B2 | 11/2009 | Raksi et al. | |
| 8,070,290 B2 | 12/2011 | Gille et al. | |
| 2001/0021844 A1 | 9/2001 | Kurtz et al. | |
| 2002/0103481 A1 | 8/2002 | Webb et al. | |
| 2002/0103482 A1 | 8/2002 | Scholler et al. | |
| 2003/0153904 A1 | 8/2003 | Patel | |
| 2004/0070761 A1 | 4/2004 | Horvath et al. | |
| 2004/0254568 A1 | 12/2004 | Rathjen | |
| 2005/0143718 A1 | 6/2005 | Rathjen | |
| 2005/0154408 A1 | 7/2005 | Dybbs | |
| 2006/0179992 A1 | 8/2006 | Kermani | |
| 2006/0195078 A1 | 8/2006 | Webb et al. | |
| 2006/0261502 A1 | 11/2006 | Platt et al. | |
| 2007/0093795 A1 | 4/2007 | Melcher et al. | |
| 2007/0093796 A1 | 4/2007 | Raksi et al. | |
| 2007/0173791 A1 | 7/2007 | Raksi | |
| 2007/0253083 A1 | 11/2007 | Muhlhoff et al. | |
| 2008/0071254 A1* | 3/2008 | Lummis et al. | 606/4 |
| 2008/0194915 A1 | 8/2008 | Blackhurst et al. | |
| 2009/0069794 A1 | 3/2009 | Kurtz | |
| 2009/0137989 A1 | 5/2009 | Kataoka | |
| 2009/0163898 A1 | 6/2009 | Gertner et al. | |
| 2009/0182310 A1 | 7/2009 | Gertner et al. | |
| 2011/0166535 A1 | 7/2011 | Hasegawa et al. | |
| 2011/0190739 A1 | 8/2011 | Frey et al. | |
| 2011/0190741 A1 | 8/2011 | Deisinger et al. | |
| 2011/0319873 A1 | 12/2011 | Raksi et al. | |

FOREIGN PATENT DOCUMENTS

| | | |
|---|---|---|
| EP | 0536951 B1 | 8/1997 |
| EP | 0634947 B1 | 12/2001 |
| EP | 1982640 | 10/2008 |
| WO | 8803396 A1 | 5/1988 |
| WO | 8906519 A2 | 7/1989 |
| WO | 2011163507 A2 | 12/2011 |

OTHER PUBLICATIONS

International Search Report for corresponding International Application No. PCT/US2012/049319 with mailing date Nov. 19, 2012, 4 pages.

International Search Report for corresponding International Application No. PCT/US2012/052460 with mailing date Dec. 11, 2012, 6 pages.

Chinn, S. R., et al., Optical coherence tomography using a frequency-tunable optical source, Optics Letters, Mar. 1, 1997, pp. 340-342, vol. 22, No. 5.

Huber, R., et al., Three-dimensional and C-mode OCT imaging with a compact, frequency swept laser source at 1300 nm, Optics Express, Dec. 26, 2005, pp. 10523-15038, vol. 13, No. 26.

International Search Report and Written Opinion dated Mar. 19, 2009 for International Application No. PCT/US2008/075902, filed Sep. 10, 2008, 8 pages.

Yun, S. H., et al., Wavelength-Swept Fiber Laser with Frequency Shifted Feedback and Resonantly Swept Intra-Cavity Acoustooptic Tunable Filter, IEEE Journal of Selected Topics in Quantum Electronics, Aug. 1997, pp. 1087-1096, vol. 3, No. 4.

International Search Report dated Sep. 5, 2012 for corresponding International Application No. PCT/US2012/036546, 3 pages.

International Search Report dated Feb. 29, 2012 for corresponding International Application No. PCT/US2011/041676, 3 pages.

International Search Report for corresponding International Application No. PCT/US2012/070781 with mailing date Mar. 25, 2013, 3 pages.

* cited by examiner

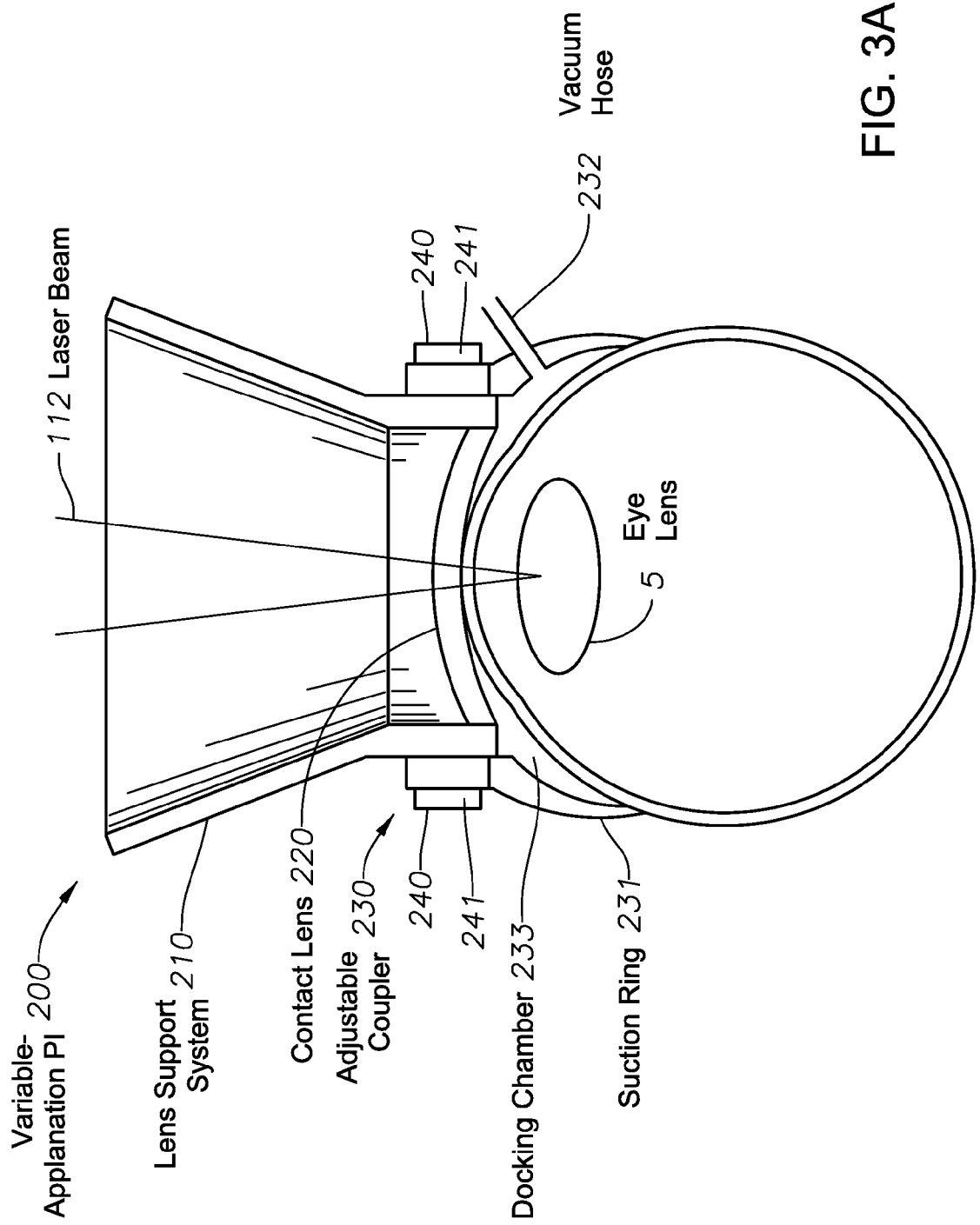

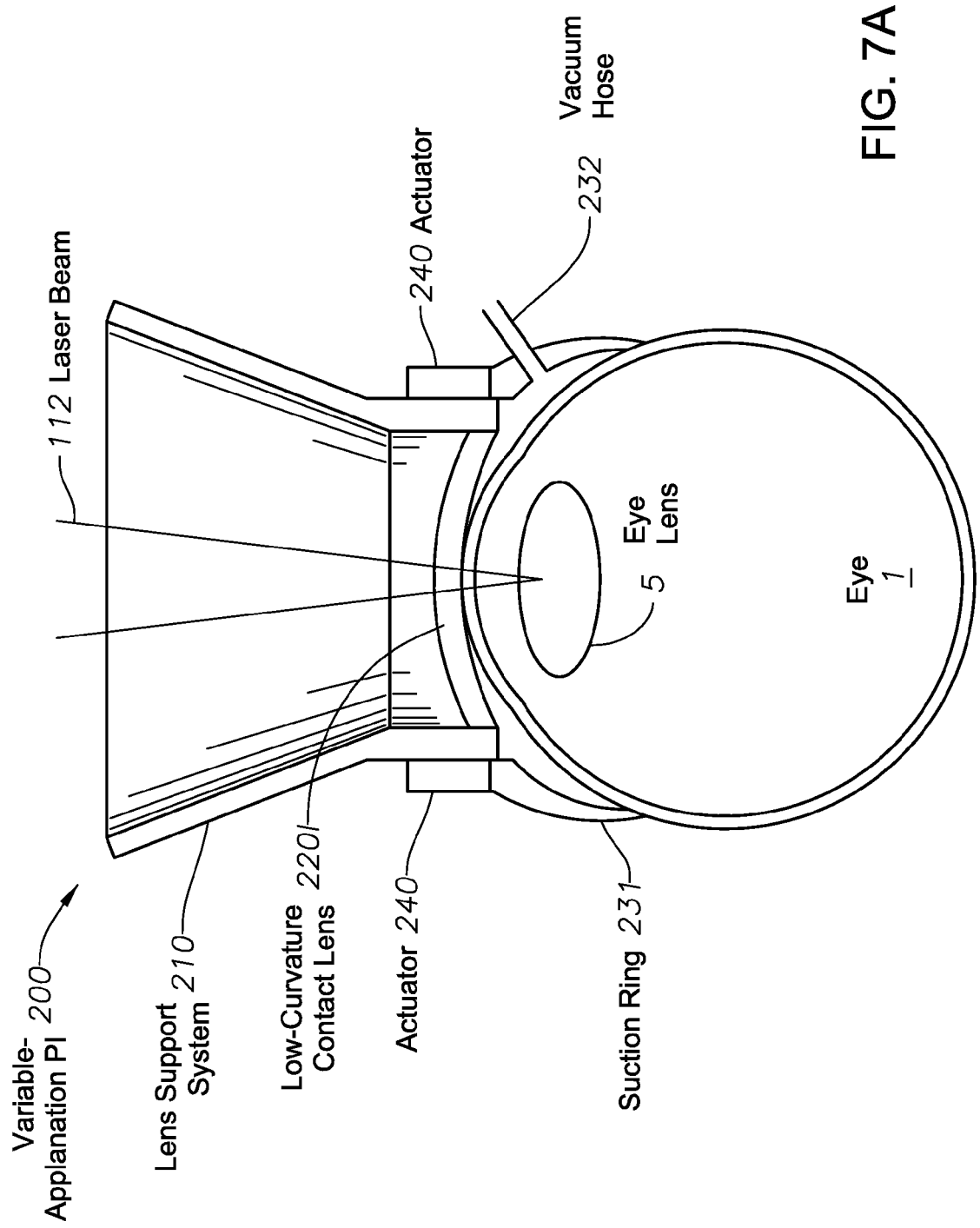

PATIENT INTERFACE WITH VARIABLE APPLANATION

TECHNICAL FIELD

This patent document relates to patient interfaces for ophthalmic surgery. More precisely, this patent document relates to patient interfaces with variable applanation for multi-step ophthalmic surgical procedures.

BACKGROUND

Many ophthalmic surgical procedures can be performed by photodisrupting or cutting the targeted ophthalmic tissue with a laser beam of femtosecond pulses. The cuts can be created by scanning the focus spot of the laser beam in a two or three dimensional scan-pattern. Each femtosecond pulse can create a plasma or cavitation bubble at the focus spot of the laser. A layer of these microscopic bubbles can separate the targeted tissue into two parts, creating a macroscopic surgical cut. A volume of these bubbles can cause a volumetric photodisruption of the target tissue.

The minimum pulse energy density capable of creating the plasma in a tissue is called the plasma threshold. The plasma threshold is specific for each ophthalmic tissue. Pulses with energy density below the plasma threshold do not create bubbles. On the other hand, pulses with energy density substantially exceeding the plasma threshold can cause collateral damage and unwanted thermal effects in the target tissue. Therefore, existing ophthalmic surgical systems are typically designed to deliver laser pulses with energy density exceeding the plasma threshold, but only moderately. Such systems can create the desired cuts in the target tissue with limited or minimal thermal effects and collateral damage caused by the excess energy of the laser pulses.

Even if the system was designed to deliver a laser beam with energy density exceeding the plasma threshold along the entire scan-pattern, in real-life situations the energy density of the laser beam can dip below the plasma threshold along a portion of the scan-pattern. In those portions the target tissue will not be photodisrupted or cut, diminishing the efficacy of the ophthalmic surgical procedure. Therefore, it is a high priority challenge to design surgical laser systems that can keep the energy density of the laser beam slightly above the plasma threshold throughout the complete scan-patterns of ophthalmic surgical processes.

Several factors impact the energy density of the laser beam. The energy density is proportional to the peak intensity of the laser beam at the focus spot and inversely proportional to the area of the focus spot. The area of the focus spot is typically of the order of a $(2\text{-}5 \text{ micrometers})^2$. This focus-spot-area depends on the numerical aperture of the laser beam, on the quality of the optics of the surgical laser system and on the scattering the laser beam experiences while traveling through the ophthalmic tissue after it left the optics, among others. The area of the focus spot cannot be reduced below its diffraction-limited value, set by the wave nature of light. In principle, some of the most efficient optics are capable of delivering their laser beam with a focus spot close to the diffraction limited value throughout the scan-pattern within the surgical volume.

Unfortunately, in reality the laser beams often fall short of being diffraction limited in at least parts of the scan-pattern due to distortions in the laser beam itself, distortions in the beam scanning-focusing optics and distortions in the tissue itself. Therefore, it remains a challenge to design systems and methods that reduce and minimize the beam distortions even in real-life applications so that the laser beam can be delivered with an energy density that exceeds the plasma threshold throughout the entire scan-pattern but only by a small amount during ophthalmic surgeries.

SUMMARY

Femtosecond laser ophthalmic surgery is now used for a variety of ophthalmic procedures, including corneal flap creation for LASIK procedures, intrastromal surgery, and cataract surgery, among others. These surgeries involve creating incisions, cuts, and photodisruption at different locations in the cornea, the lens capsule and the lens. In particular, a first stage of a cataract surgery can include a capsulotomy in the lens capsule and a photodisruption, lens lysis, lens chop or a cataract procedure in the crystalline lens. The lens is located in a deep central region of the eye: at large $z_c$ depths in the range of 3-10 mm but laterally within a limited central radius $r_c$ in the range of 2-5 mm or 3-4 mm. Here, the $z_c$ depth can be measured from the apex of the eye where the cornea meets the optics of the laser system, and the lateral radius $r_c$ can be measured from an optical axis of the eye or the laser system.

The first stage of the cataract surgery can be followed by a second stage concentrating on the cornea that can involve forming entry cuts, access cuts, limbal relaxing incisions, arcuate incisions, or a hinged flap in the cornea. These cuts can be formed in a shallow peripheral corneal region: at smaller $z_p$ depths of 0-2 mm but at greater peripheral radii between $r_c$ and $r_p$, where the peripheral radius $r_p$ can be in the range of 4-9 mm or 5-8 mm.

Many ophthalmic surgical laser systems increase the targeting precision of the laser beam by docking a patient interface (PI) onto the eye to immobilize it. The patient interface typically includes a contact lens, in direct contact with the cornea to guide the laser beam from the system optic into the ophthalmic tissue. The formation of a contact surface between the contact lens of the patient interface and the cornea is often termed an applanation. The patient interface can also include a suction ring that is attached to the eye by vacuum suction. As the PI is lowered onto the eye, vacuum suction can be applied to the suction ring so that the atmospheric pressure presses the patient interface and thus the contact lens onto the eye.

Most cataract surgeries start by docking the PI onto the cornea to immobilize the eye. This docking is followed by performing calibrating measurements of the target regions to guide the surgical laser beam precisely, after which the first and second stages of the surgical procedures are carried out. During the entire surgical process the docking is not released to keep the eye in place. This allows the use of the initial calibration throughout the surgical process and avoids the need to re-dock the PI, which could be a quite time consuming extra step.

Unfortunately, as the pressure applied by the patient interface to the eye increases during applanation, it can deform the ophthalmic tissues of the eye and the boundaries separating them. And since the indices of refraction of different tissues are different, as the laser beam passes through the deformed boundaries of the deformed ophthalmic tissues on its way to the target region, it suffers distortions that were not included into the system design calculations. These uncalculated distortions can increase the size of the focus spot to such a degree that the energy density of the laser beam is driven below the plasma threshold, preventing the proper cutting of the target tissues and thus qualitatively diminishing the efficiency of the surgery.

In the specific example of a capsulotomy, high pressure by the PI can wrinkle the cornea. Since the index of refraction of the corneal tissue is different from that of the aqueous humor behind it, the laser beam can suffer enhanced distortions at the wrinkled cornea-aqueous humor boundary on its way to the lens, driving its energy density below the plasma threshold. Such a weakened beam may not be able to cut the lens capsule, leaving partially connected tissue behind and thus making the capsulotomy incomplete. Incomplete capsulotomy requires additional cutting by the surgeon with mechanical tools that have substantially lower precision and can introduce undesirable tissue tearing.

In addition to the reduction of the beam energy density, the corneal wrinkling also reorients the corneal-aqueous humor interface, potentially misdirecting the laser beam from its intended target.

Finally, the pressure of the patient interface can introduce other types of undesirable consequences as well, such as a shifting and tilting of the targeted lens, an additional mechanism causing the laser beam to miss its intended target.

Therefore, laser systems and surgical methods that reduce the pressure of the patient interface on the cornea can reduce the negative effects of the above three problems and thus offer improved surgical precision and performance.

The problems associated with the pressure of the PI wrinkling the cornea can be reduced by recognizing that the wrinkling has a negative effect only if the beam is directed to cross the wrinkled corneal boundary on its way to a target region beyond the cornea, since only for such beam pathways does the wrinkled corneal boundary distort the beam, reducing its energy density.

To capitalize on this recognition, it is recalled that the beam is directed and scanned beyond the cornea only during the first stage of the cataract surgery, when the capsulotomy and lens photodisruption are performed. Remarkably, in this first stage, while the beam is scanned at large z depths, it is scanned only in the central region of the eye within the central radius $r_c$ in the range of 2-5 mm or 3-4 mm. Therefore, the first stage of the cataract surgery can be performed by the patient interface making only a partial contact with the cornea, limited to the central region. Notably, such a partial contact can be formed by applying only a partial pressure, less than the full pressure needed to force a full contact with the central and the peripheral region of the cornea.

In sum, the corneal wrinkling can be reduced and thus the energy density can be kept above the plasma threshold throughout the first stage of the cataract surgery by patient interfaces that can apply only a partial pressure to form only a partial contact between the eye and the patient interface during the first stage, followed by the formation of an extended or full contact with increased or full pressure for the second stage of the cataract surgery. The negative consequences of the wrinkling caused by the full pressure in the second stage could be greatly diminished as the laser beam is scanned through scan-patterns only within the cornea in this second stage, thus the beam does not cross the deformed cornea-aqueous humor boundary before it hits its target within the scan-pattern.

The above recognition, however, cannot be put to good use with today's rigid patient interfaces, because in the existing systems once the PI is firmly docked in place, the docking cannot and should not be varied anymore. This is because should the docking be released between the first and second stages of the cataract surgery to increase the applanation from partial to full, a re-docking of the PI would be required, necessitating a recalibration of the measurements and surgical planning, as well as increasing the surgical procedure time: both substantial drawbacks.

In contrast, if the applanation of a new type of patient interface were variable without releasing the docking, then the first phase of the cataract surgery could be performed with only a partial applanation, during which the PI only contacted the central part of the cornea within the contact radius of $r_c$ in the range of 2-5 mm or 3-4 mm. Such a partial applanation could be achieved by applying only a partial pressure, leading to limited or no corneal wrinkling, thereby avoiding the beam energy density dipping below the plasma threshold, the beam misdirection, and the lens-shifting.

After the capsulotomy and the lens photodisruption of the first stage is substantially completed, the applanation of such a variable-applanation patient interface could be increased from partial to full or extended for the second stage of the cataract surgery without releasing the docking. The full or extended applanation can be achieved by increasing the pressure to full to increase the contact radius from the central radius of $r_c$ to the peripheral radius of $r_p$ in the range of 4-9 mm or 5-8 mm. While the increase to full pressure probably wrinkles the cornea-aqueous humor interface, this wrinkling causes only limited or no deterioration of the surgical performance, as in the second stage of the cataract surgery the cuts are formed only within the corneal tissue and thus the laser beam does not have to propagate through the wrinkled cornea-aqueous humor interface before hitting its target within the scan-pattern.

In an alternative method of using such variable-applanation patient interfaces, the above first and second surgical stages can be performed in reverse order. The surgeon can start by performing the peripheral corneal cuts first and the central cuts in the lens and the capsule second. With such methods the variable-applanation patient interface can be first coupled to the eye with full pressure for the corneal stage of the surgery, followed by reducing the pressure to a partial value and performing the lens photodisruption and capsulotomy with reduced or no wrinkling of the cornea.

In sum, the above considerations demonstrate that new types of patient interfaces that can vary their applanation during cataract surgery could avoid or substantially reduce the three listed disadvantages of some of today's rigid patient interfaces: the reduction of the energy density, the misdirection of the laser beam and the shifting of the lens.

Broadly and generally, this patent document describes such new types of variable-applanation patient interfaces. Embodiments of these variable-applanation patient interfaces can include a lens support system, attachable to a distal end of an ophthalmic surgical laser system; a contact lens, supported by the lens support system, configured to make contact with an eye-surface; and an adjustable coupler, coupled to at least one of the lens support system and the contact lens, and configured to be coupled to a non-central region of the eye-surface, to accommodate the contact lens to contact a central region of the eye-surface with a central applanation, to accommodate the contact lens to contact an extended region of the eye-surface larger than the central region with an extended applanation, and to enable a change between the central applanation and an extended applanation.

In other embodiments, a variable-applanation patient interface can comprise a lens support system, attachable to a distal end of an ophthalmic surgical laser system, the lens support system configured to support a central contact lens, configured to contact a central region of the eye-surface with a central applanation, to enable an exchange of the central contact lens to an extended contact lens, and to support the extended contact lens, configured to contact an extended region of the eye-surface larger than the central region with an extended applanation; and an adjustable coupler, couplable to at least one of the lens support system, the central contact lens and the extended contact lens, and configured to be coupled to a non-central region of the eye-surface.

In other embodiments, a method of ophthalmic surgery can include attaching a lens support system to a distal end of an ophthalmic surgical laser system; coupling an adjustable coupler to a peripheral region of an eye-surface, the adjustable coupler being coupled to at least one of the lens support system and a contact lens; coupling the contact lens to a central region of the eye-surface, the contact lens having a central applanation and being supported by the lens support system; enabling a change between the central applanation and an extended applanation by the adjustable coupler; and coupling the contact lens to an extended region of the eye-surface larger than the central region with the extended applanation.

In yet other embodiments, a method of ophthalmic surgery can include attaching a lens support system to a distal end of an ophthalmic surgical laser system; coupling an adjustable coupler to a peripheral region of an eye, the adjustable coupler being coupled to at least one of the lens support system and a contact lens; coupling the contact lens to the eye with an applanation; and varying the applanation of the contact lens while preserving the coupling of the adjustable coupler to the eye.

BRIEF DESCRIPTION OF DRAWINGS

FIGS. 3A-B illustrate an embodiment of a variable applanation patient interface with an actuator.

FIGS. 7A-B illustrate an embodiment of a variable applanation patient interface.

DETAILED DESCRIPTION

This patent document describes embodiments of a variable-applanation patient interface (VA-PI) that can reduce the wrinkling of the corneal tissue during ophthalmic procedures.

Figure 1:
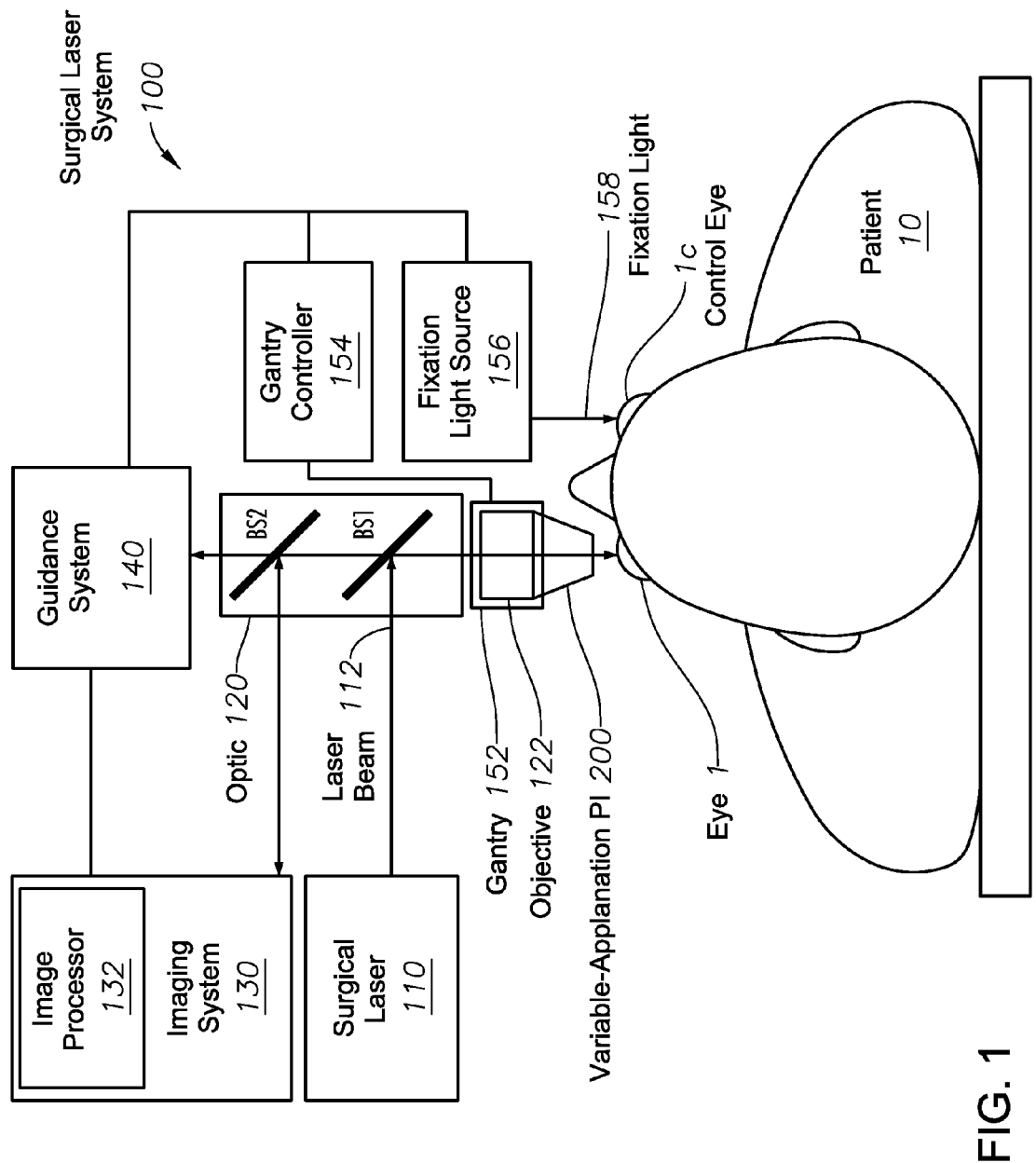
FIG. 1 illustrates an ophthalmic surgical laser system.

FIG. 1 illustrates an ophthalmic surgical laser system 100. The ophthalmic surgical laser system 100 can include a surgical laser 110 that can generate and couple a surgical laser beam 112 into an optic 120 at a beam splitter BS1. The surgical laser 110 can be capable of generating a pulsed laser beam with a pulse length in the femtosecond or picosecond range. The optic 120 can redirect and deliver the pulsed laser beam 112 into an eye 1 of a patient 10 through an objective 122 and a variable-applanation patient interface VA-PI 200.

The laser system 100 can also include an imaging system 130. The imaging system 130 can provide one or more images for the ophthalmic surgeon to increase the precision of the ophthalmic procedure. The image can include a stereoscopic microscope image, a video-image, a Scheimpflug image, or an Optical Coherence Tomographic (OCT) image. The image can be analyzed by an image processor 132.

The generated image can be displayed on a guidance system 140 to provide guidance information for the surgeon. One of the functions of the guidance system 140 can be to guide the surgeon to align a center of the eye 1 and a center or axis of the optic 120 for optimizing the docking. In some embodiments, the guidance system 140 can include a video-monitor to display a video image of a video microscope. In others, the guidance system can include an OCT display to display an OCT image created by the imaging system 130. In yet others, the guidance system 140 can display both a video image and an OCT image.

In addition, the guidance system 140 can include a guidance display to guide the surgeon based on the result of the processing of the image by the image processor 132. For example, the guidance display of the guidance system 140 can include a target pattern or a crosshair pattern overlaid on the video image of the eye 1 to indicate a position of an optical center or axis of the optic 120, thus allowing the surgeon to determine the position of the eye 1 relative to the axis of the optic 120. In other systems, the guidance system 140 can display one or more arrows to suggest the surgeon a corrective action to align the optic 120 and the eye 1.

The correction of the alignment can be initiated either by the surgeon or by a processor of the surgical laser system 100, in response to the guidance information displayed by the guidance system 140. For example, some embodiments of the laser system 100 can include a gantry 152 and a gantry controller 154 to move the objective 122 laterally and align it with a center of the eye 1 as part of the docking procedure. The movement of the gantry 152 can compensate a lateral or transverse misalignment of the eye 1 and the optic 120.

A rotational or angular misalignment of the eye 1 and the optical axis of the optic 120 can be compensated by a fixation light source 156 that projects a fixation light 158 into a control eye 1c. The patient 10 can be instructed to follow the movement of the fixation light 158. As the surgeon adjusts the fixation light 158, he or she can follow the movement of the video image of the eye 1 relative to the target pattern and the optical axis of the optic 120 on the guidance display of the guidance system 140 and continue to adjust the fixation light 158 until the eye 1 is aligned with the optical axis of the optic 120 to the desired degree.

Figure 2A:
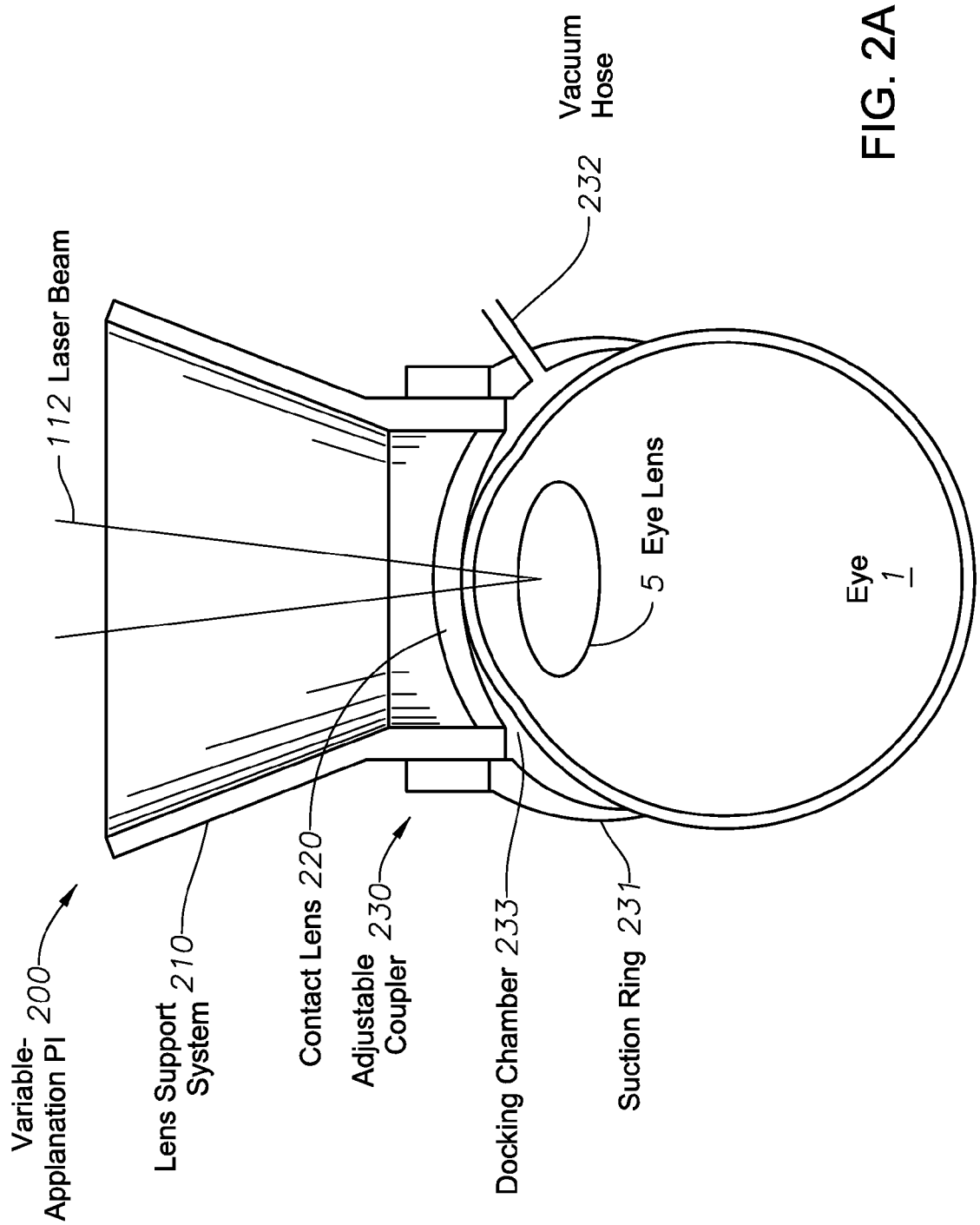
FIGS. 2A-B illustrate a variable applanation patient interface.
Figure 2B:
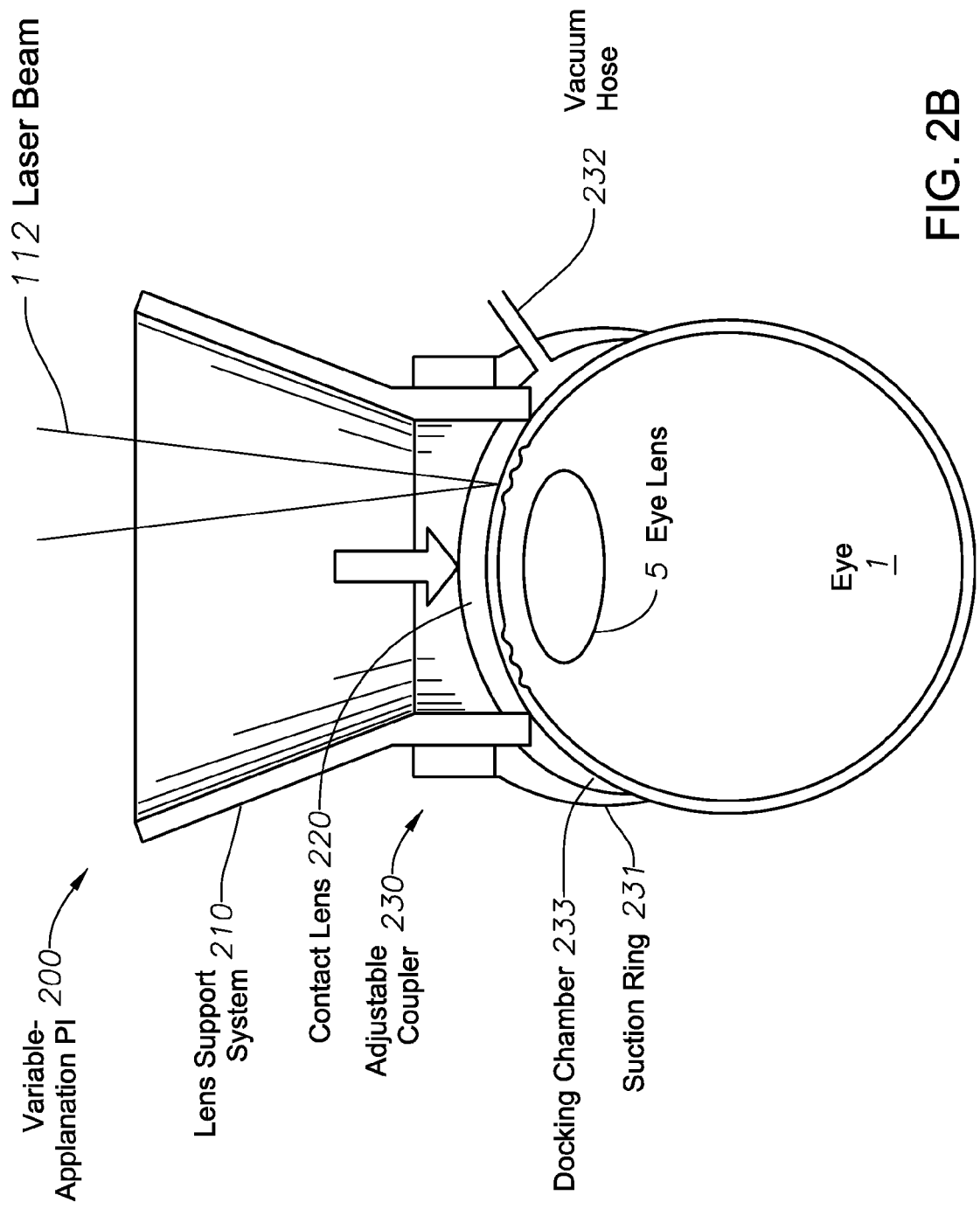

FIGS. 2A-B illustrate an embodiment of the variable-applanation patient interface (VA-PI) 200 that can include a lens support system 210, attachable to a distal end of the ophthalmic surgical laser system 100 such as the objective 122; a contact lens 220, supported by the lens support system 210 and configured to make contact with an eye-surface such as the cornea. The VA-PI 200 can further include an adjustable coupler 230 that can be coupled to at least one of the lens support system 210 and the contact lens 220. The adjustable coupler 230 can be configured to be coupled to a non-central or peripheral region of the eye-surface, to accommodate the contact lens 220 to contact a central region of the eye-surface with a central applanation, to accommodate the contact lens 220 to contact an extended region of the eye-surface larger than the central region with an extended applanation, and to enable a change between the central applanation and the extended applanation. The extended region can include the central region and the peripheral region of the eye-surface. The eye-surface can extend beyond the cornea of the eye.

Using the here-described VA-PI 200 design can minimize the corneal wrinkling in the first stage of a cataract surgery when the laser beam 112 is applied only to a lens 5 of the eye 1 to perform a cataract procedure, a capsulotomy, a lens lysis, a photodisruption, or a lens chop. Therefore, using embodiments of the VA-PI 200 during the first stage of cataract surgeries can avoid the energy density dropping below the plasma threshold anywhere along the scan-pattern, the laser beam getting misdirected by the wrinkled cornea-aqueous humor interface, and the lens 5 getting shifted and rotated. For all these reasons, using embodiments of the VA-PI 200 can increase the precision and efficiency of cataract surgeries.

The VA-PI 200 with such an adjustable coupler 230 can enable the change between the central applanation and the extended applanation of the contact lens 220 during, or as part of the ophthalmic surgery, without releasing the coupling of the adjustable coupler 230 to the non-central or peripheral region of the eye-surface. The maintaining of the coupling can be advantageous as re-establishing the coupling or re-docking after releasing can be a time consuming and imprecise procedure while time is at a premium during ophthalmic surgery.

In some embodiments of the VA-PI 200, the adjustable coupler 230 being configured to enable a change between the central applanation and the extended applanation can include the adjustable coupler 230 being configured to enable a change from the central applanation to the extended applanation, or a change from the extended applanation to the central applanation.

In some embodiments of the VA-PI 200, the adjustable coupler 230 can be integrated with the lens support system 210. In some cases, the adjustable coupler 230 can be part of the lens support system 210.

In some embodiments, the adjustable coupler 230 can include a suction ring 231 that can form an airtight contact with the eye-surface and a vacuum hose 232 to connect a suction pump (not shown) with a docking chamber 233, formed by the contact lens 220, the suction ring 231, and the eye-surface. The suction ring 231 can include a ring, a skirt, a cone, or any other structure capable of providing an airtight coupling to the eye-surface.

As discussed before, such a VA-PI 200 can make it possible for the contact lens 220, when making contact with the central region of the eye-surface, to enable the ophthalmic surgical laser system 100 to perform a cataract laser procedure, a capsulotomy, a lens lysis, a photodisruption, or a lens chop of a lens of the eye. Further, such a VA-PI 200 can make it possible for the contact lens 220, when making contact with the extended region of the eye-surface, to enable the ophthalmic surgical laser system 100 to form a limbal relaxing incision, an arcuate incision, an anterior chamber access cut, an anterior chamber entry cut, a flap-cut or a corneal refractive procedure. As before, the central radius $r_c$ of the central region can be in the range of 2-5 mm, in some embodiments in the range of 3-4 mm, whereas the peripheral radius $r_p$ of the peripheral region can be in the range of 4-9 mm, in some embodiments in the range of 5-8 mm.

FIG. 2A illustrates that in the first stage of the cataract surgery, when the laser beam 112 is applied only to the lens 5, the VA-PI 200 can be brought into contact only with a central portion of the cornea with a central radius $r_c$, and therefore the corneal tissue may wrinkle only a little or not at all.

FIG. 2B illustrates that, in contrast, when during the second stage of the cataract surgery a higher pressure is applied to increase the contact radius from the central $r_c$ radius to the peripheral $r_p$ radius, the corneal tissue may get wrinkled substantially, as shown. While this wrinkling could have lead to one or more of the above three problems for a capsulotomy or cataract procedure, it is of little significance for the corneal procedures that are performed in the second stage, since in this second stage the laser beam is directed only to corneal targets and thus the laser beam is not crossing the wrinkled boundary before hitting its target.

As before, in some embodiments the order of performing the first and second surgical stages can be interchanged. Accordingly, the VA-PI 200 can be first used with a higher pressure, resulting in the contact lens 220 contacting the extended region of the eye-surface, followed by reducing the pressure, resulting in the contact lens 220 making contact only with the central region of the eye-surface.

In some embodiments of the VA-PI 200 the applanation can be adjusted manually by the surgeon. For example, the VA-PI 200 can include a positioning mechanism that can stabilize the lens support system 210 in a range of positions, wherever the surgeon adjusts it. The positioning mechanism can be based on mechanical friction, adjustment screws, lever arms, or a wide variety of locking mechanisms.

Figure 3B:
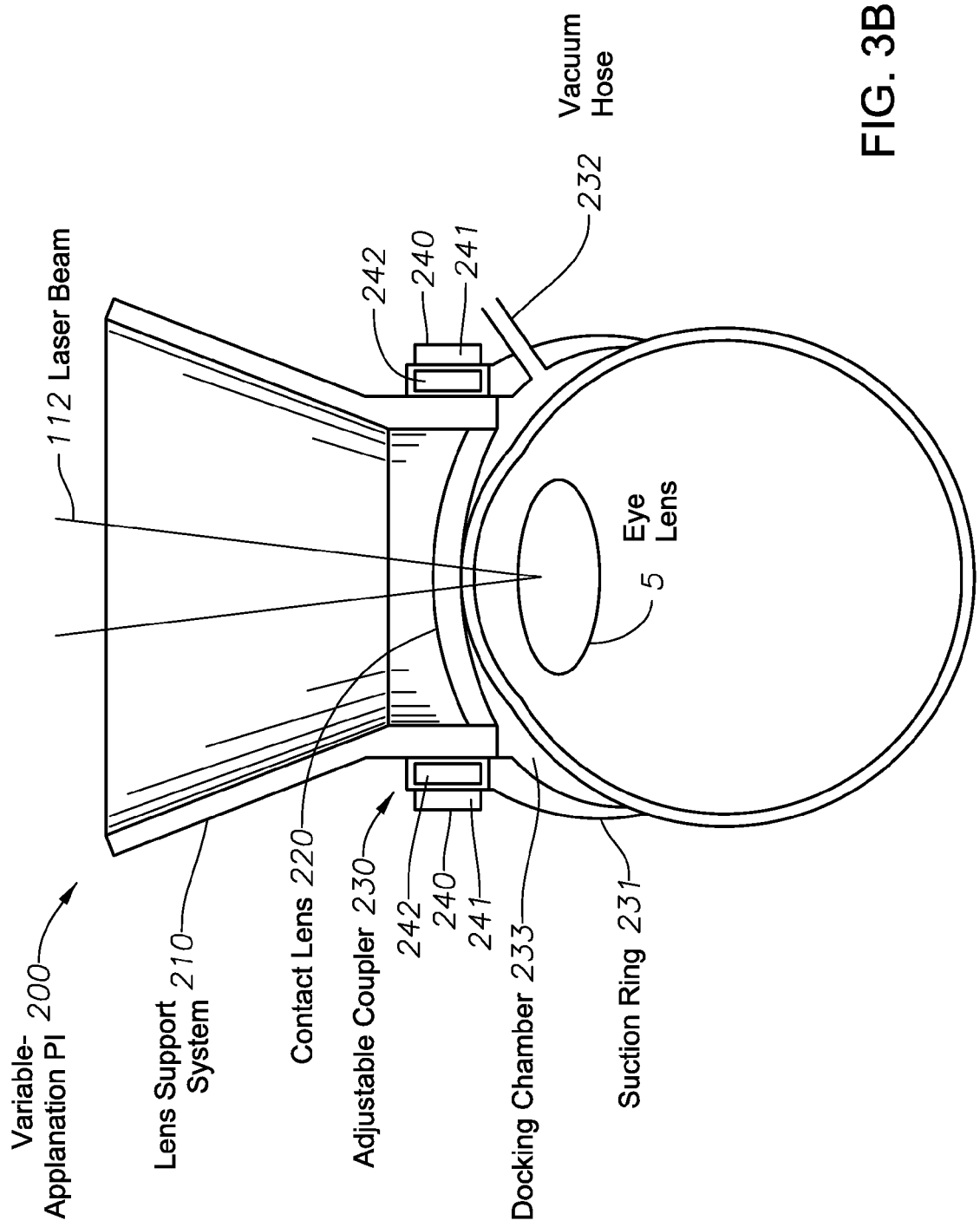

FIGS. 3A-B illustrate that in other embodiments the ophthalmic surgical laser system 100 can include an actuator 240 to adjust the applanation. The actuator 240 can be coupled to the lens support system 210, the adjustable coupler 230, the contact lens 220, or any combination of these. The actuator 240 can include a mechanical, a friction-based, a spring-loaded, an adhesive-based, a pneumatic, a chemical, a thermal, a magnetic, an electric or an electromagnetic system. The actuator 240 can be energized by a motor, a piezo-electric system, an electronic control system, a spring-loaded system or an electromagnetic system. The actuator 240 can actuate the adjustable coupler 230 to enable the changing of the applanation of the contact lens 220.

FIG. 3A illustrates that in some embodiments, the actuator 240 can include an energizer-controller 241 outside the VA-PI 200, such as an electric motor, a piezo-electric actuator, a mechanical actuator, or an electromagnetic system that can move the lens support system 210 relative to the already-docked suction ring 231, thus causing the change of the applanation of the contact lens 220.

FIG. 3B illustrates that in other embodiments the energizer-controller portion 241 of the actuator 240 may remain external to the VA-PI 200, while another portion 242 of the actuator 240 can be integrated into the VA-PI 200. In such embodiments, the external portion 241 may be able to exert a force on the integrated portion 242 to change the applanation of the contact lens 220.

In some embodiments, the adjustable coupler 230 being configured to accommodate the contact lens 220 with a central applanation can include the adjustable coupler 230 being configured to position the contact lens 220 in a first lens position; the adjustable coupler 230 being configured to accommodate the contact lens 220 with the extended applanation can include the adjustable coupler 230 being configured to position the contact lens 220 in a second lens position; and the adjustable coupler 230 being configured to enable a change between the central applanation and the extended applanation can include the adjustable coupler 230 being configured to enable a repositioning of the contact lens 220 between the first lens position and the second lens position.

In embodiments that include the actuator 240, the actuator 240 can actuate the adjustable coupler 230 to enable the change between the central applanation and the extended applanation by repositioning the contact lens 220.

Here, the contact lens 220 being in the first lens position, such as positioned at a first z depth can cause the contact lens 220 to contact the eye-surface or cornea within the central radius $r_c$ in the range of 2-5 mm, or 3-4 mm that enables the ophthalmic surgical laser system 100 to carry out one of the cataract procedures listed above, whereas the contact lens 220 being in the second lens position, such as positioned at a second z depth can cause the contact lens 220 to contact the eye-surface or cornea within the peripheral radius $r_p$ in the range of 4-9 mm, or 5-8 mm that enables the ophthalmic surgical laser system 100 to carry out one of the corneal procedures listed above.

Figure 4A:
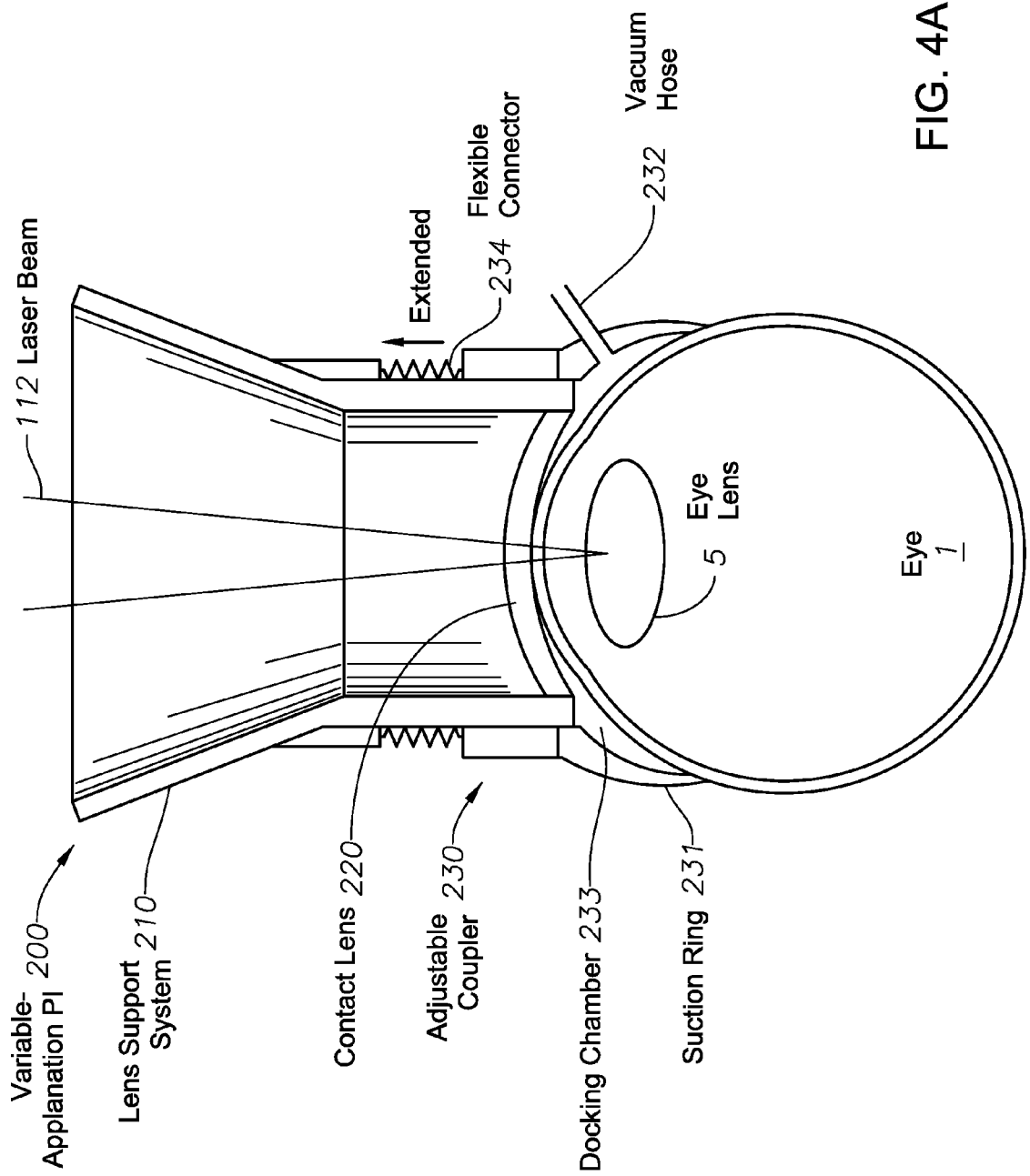
FIGS. 4A-B illustrate an embodiment of a variable applanation patient interface with a flexible connector.
Figure 4B:
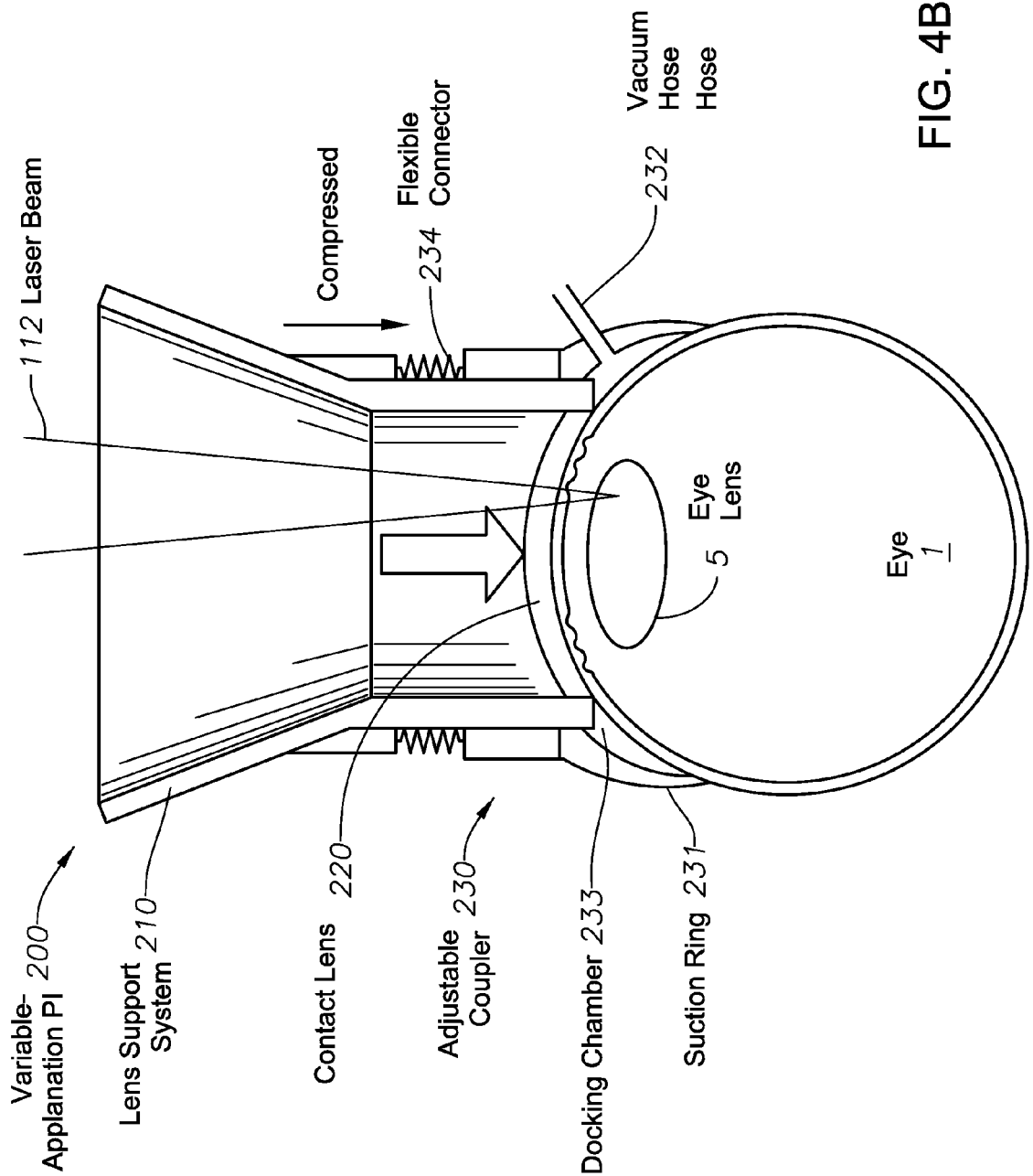

FIGS. 4A-B illustrate that some embodiments of the VA-PI 200 can be of the one-piece type and include a flexible connector 234 that may be able to connect the adjustable coupler 230 to the lens support system 210, configured to assume a first connector configuration to position the contact lens 220 in the first lens position, to assume a second connector configuration to position the contact lens 220 in the second lens position; and to be able to change configuration between the first connector configuration and the second connector configuration.

The flexible connector 234 can include a wide variety of materials, including a flexible material, a plastic, a deformable material, an elastic material, a spring-action material and a magnetic coupler.

The first connector configuration of the flexible connector 234 can be an extended configuration and the second connector position can be a compressed configuration. The flexible connector 234 can be fixed in the first and second connector configuration by a locking mechanism, a positioning mechanism, a friction based mechanism, and an electromagnetic mechanism, among others.

Figure 5A:
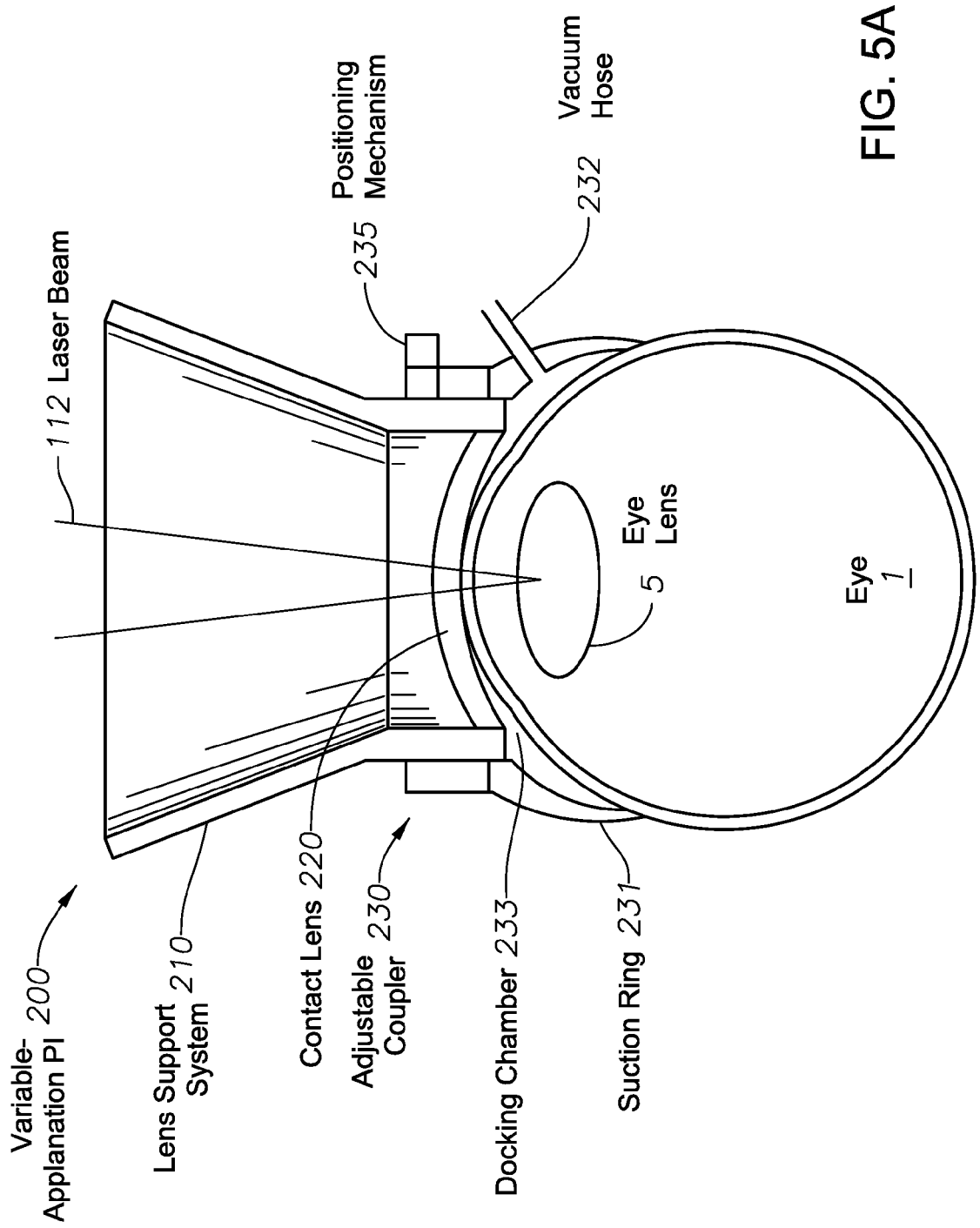
FIGS. 5A-B illustrate an embodiment of a variable applanation patient interface.
Figure 5B:
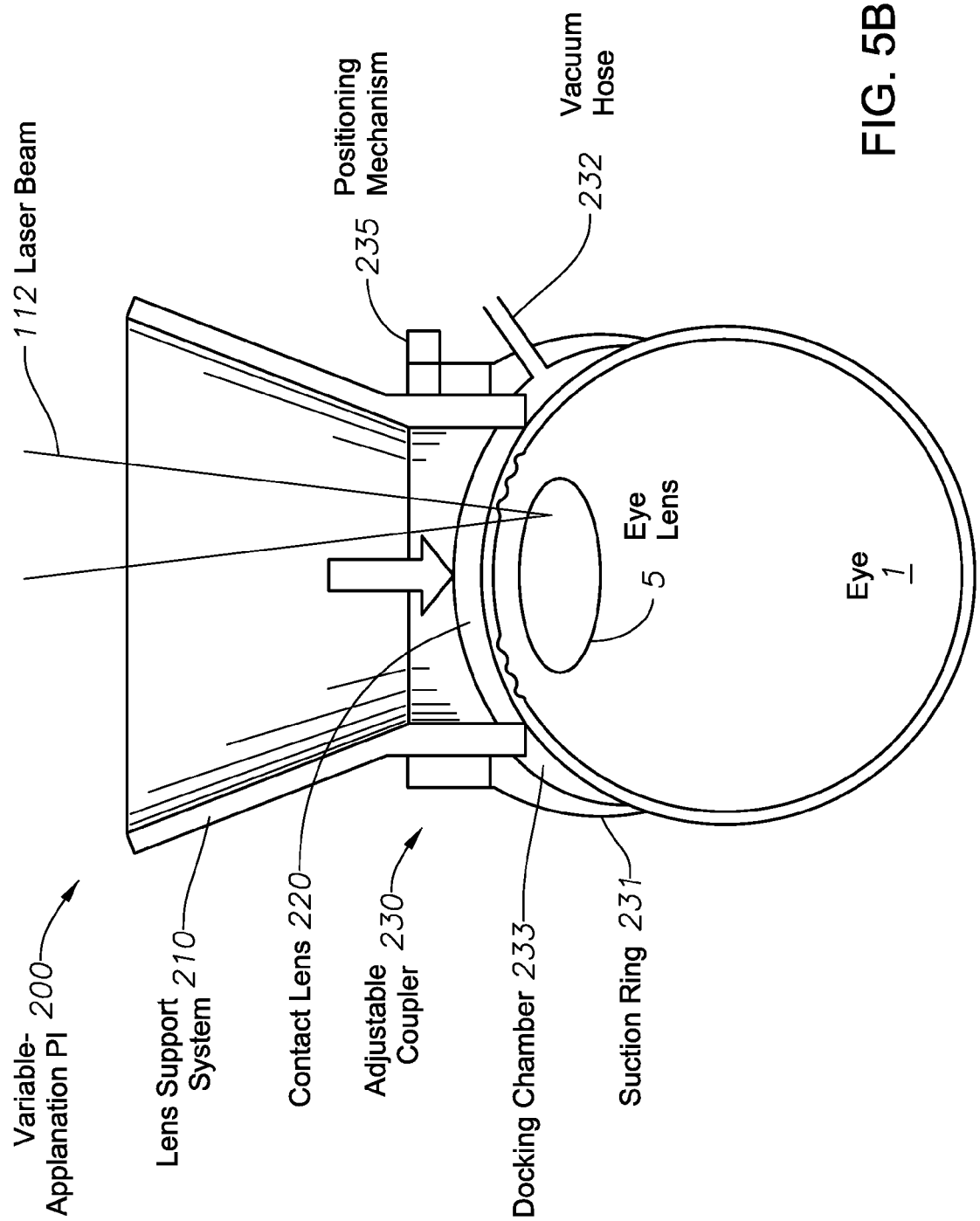

FIGS. 5A-B illustrate that some embodiments of the VA-PI 200 can be of the two-piece type, the lens support system 210 and the adjustable coupler 230 being separable or separate elements. In such embodiments the VA-PI 200 can include a positioning mechanism 235 that can be configured to accommodate the lens support system 210 and the adjustable coupler 230 to assume a first relative position to position the contact lens 220 in the first lens position, to accommodate the lens support system 210 and the adjustable coupler 230 to assume a second relative position to position the contact lens 220 in the second lens position, and to enable the lens support system 210 and the adjustable coupler 230 to change between the first relative position and the second relative position.

In some embodiments, the change between the first relative position and the second relative position of the lens support system 210 and the adjustable coupler 230 can be achieved by moving the objective 122 on which the lens support system 210 is mounted.

In an embodiment of the VA-PI 200 the adjustable coupler 230 can include a hollow cylinder that can be mated slideably to a hollow cylinder of the lens support system 210, and the positioning mechanism 235 can be configured to lock the cylinder of the lens support system 210 to the cylinder of the adjustable coupler 230 to secure the lens support system 210 in the first and second support positions.

Figure 6A:
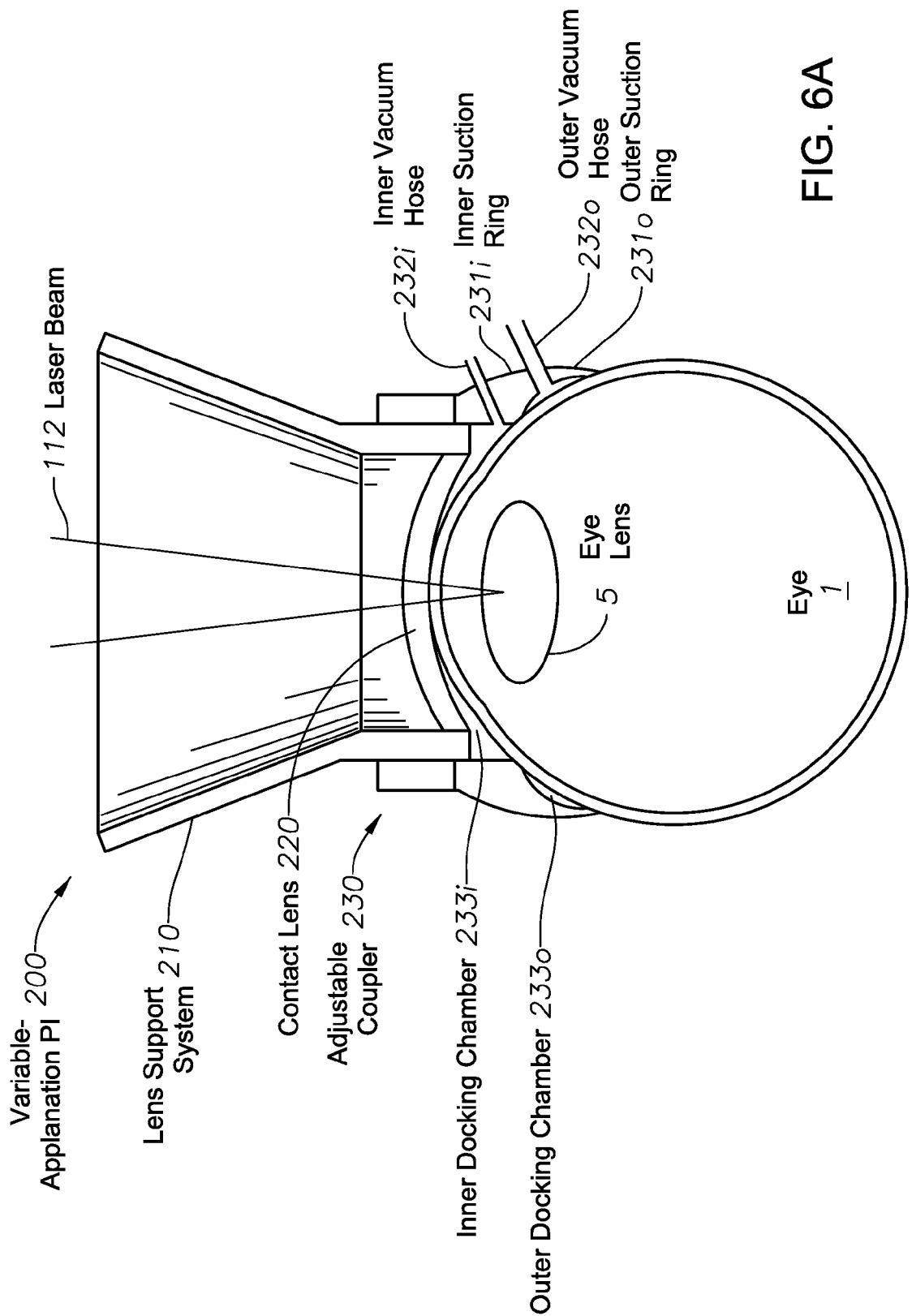
FIGS. 6A-B illustrate an embodiment of a variable applanation patient interface.
Figure 6B:
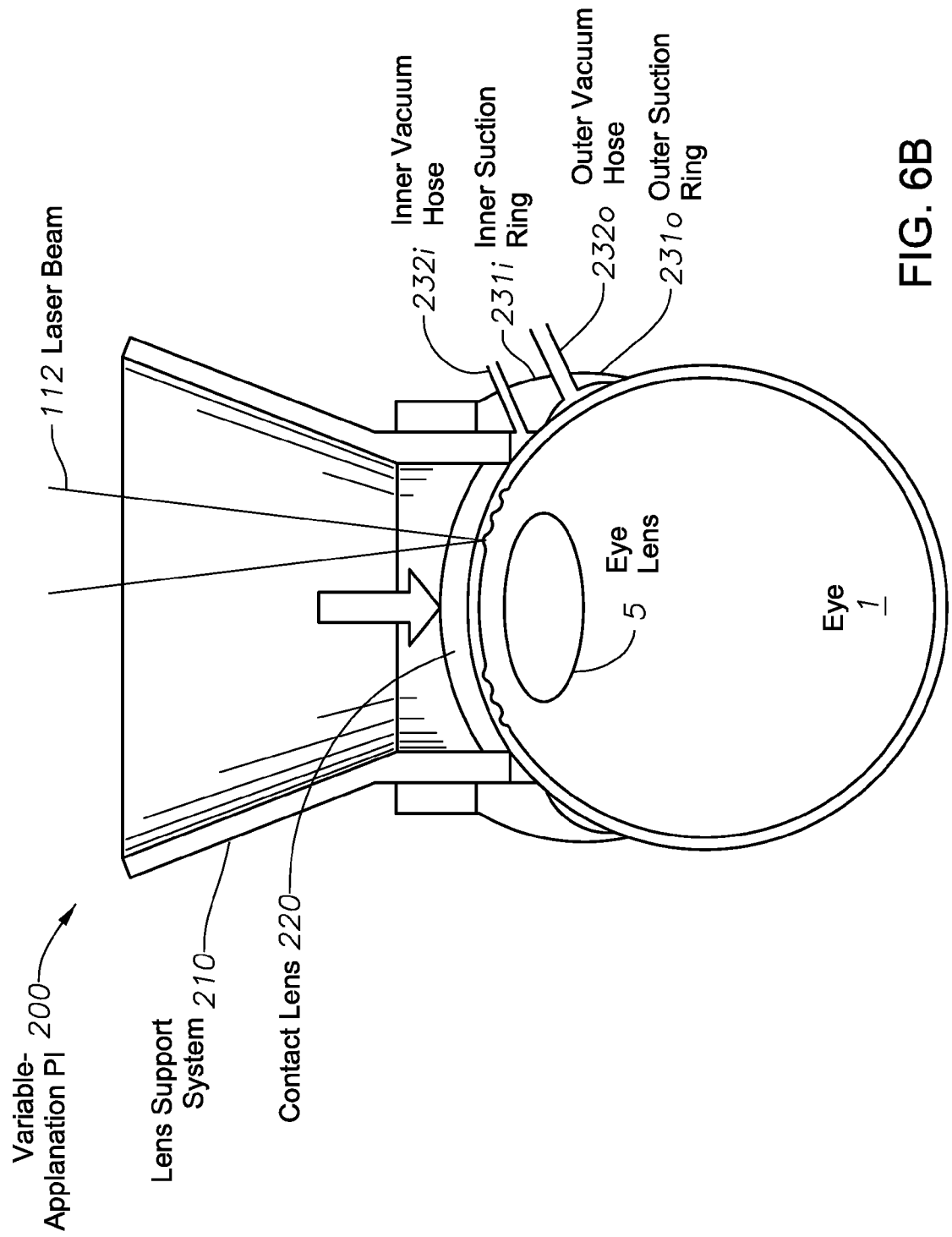

FIGS. 6A-B illustrate that in some embodiments of the VA-PI 200, the adjustable coupler 230 can include an inner suction ring 231i, defining an inner docking chamber 233i coupled to an inner vacuum hose 232i, and an outer suction ring 231o, defining an outer docking chamber 233o, coupled to an outer vacuum hose 232o. Here, the inner and outer vacuum hoses 232i and 232o can couple the corresponding inner and outer docking chambers 233i and 233o to one or more vacuum pumps (not shown). As before, the inner and outer suction rings 231i and 231o can include a ring, a skirt, a cone or any structure that can provide an airtight coupling to the eye-surface.

Such a VA-PI 200 can enable the contact lens 220 to make contact only with the central region of the eye-surface when a moderate first suction is applied to the outer docking chamber 233o through the outer vacuum hose 232o, and to make contact with the extended region of the eye-surface when an increased second suction is applied to the inner docking chamber 233i through the inner vacuum hose 232i.

The value of a first or partial pressure caused by the moderate first suction can be chosen such that the contact lens 220 contacts only the central region of the eye-surface and thus causes limited or no wrinkling of the cornea, thus minimizing the beam distortions for the cataract procedures of the first stage of the cataract surgery. The subsequent second or full pressure, caused by the increased second suction can be higher to cause the contact lens 220 to contact the eye-surface in the extended region of the eye-surface, where the extended region can include the central region and the peripheral region, as before. While the increased second or full pressure can wrinkle the cornea, the corneal procedures of the second stage of the cataract surgery may not be affected negatively by this as the laser beam is only scanned in the corneal tissue and thus does not cross the wrinkled corneal boundary on its way to the target.

Figure 7B:
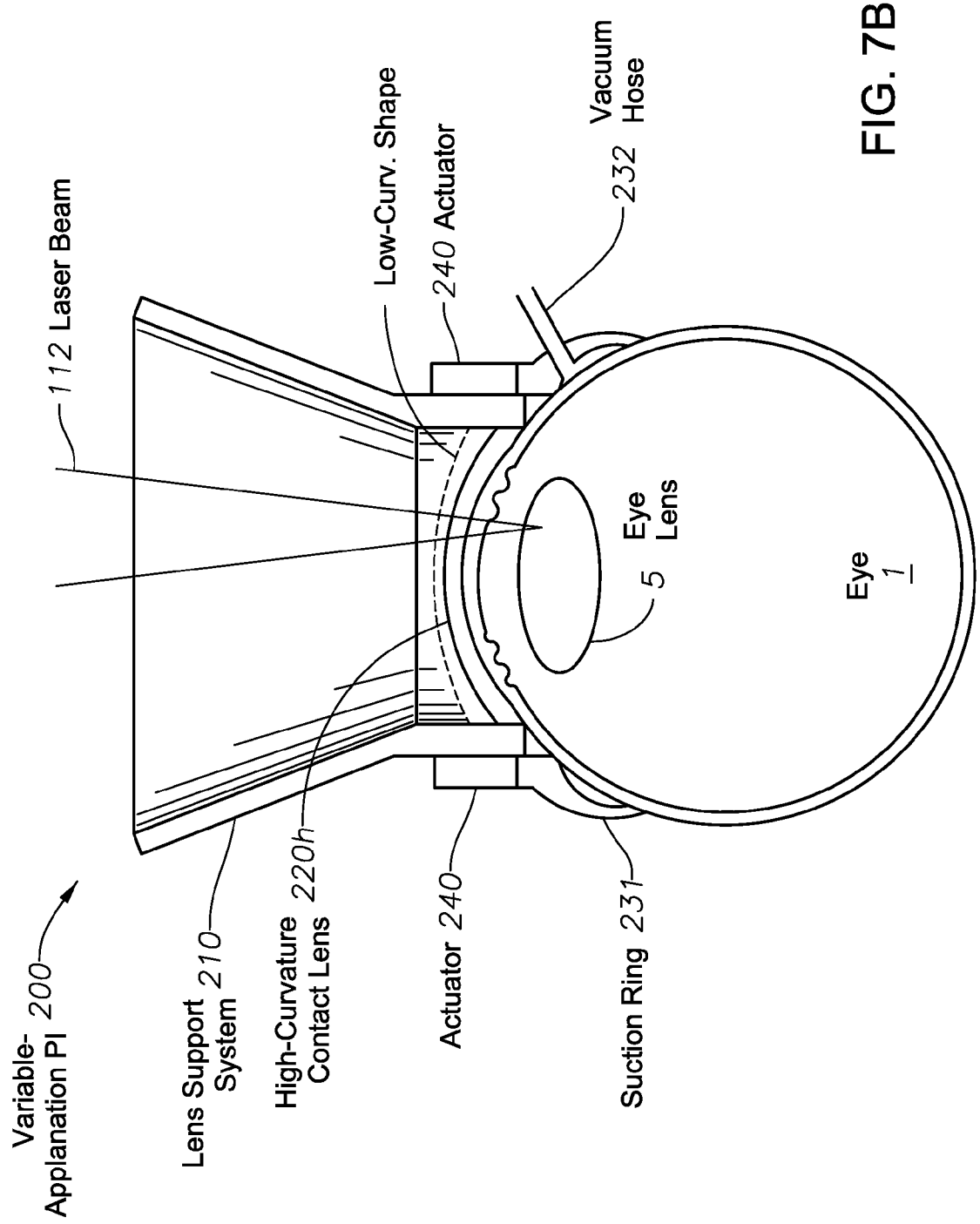

FIGS. 7A-B illustrate that in some embodiments of the VA-PI 200 the adjustable coupler 230 being configured to accommodate the contact lens 220 with the central applanation can include the adjustable coupler 230 being configured to accommodate a shape of the contact lens 220 to assume a first lens shape; the adjustable coupler 230 being configured to accommodate the contact lens 220 with the extended applanation can include the adjustable coupler 230 being configured to accommodate the shape of the contact lens 220 to assume the second lens shape; and the adjustable coupler 230 being configured to enable a change between the central applanation and the extended applanation can include the adjustable coupler 230 being configured to enable the shape of the contact lens 220 to change from the first lens shape to the second lens shape.

As shown, the first lens shape can be a low-curvature shape 220l, causing the contact lens 220 to contact the eye 1 only in the central region, whereas the second shape can be a high-curvature shape 220h that allows the contact lens 220 to contact the eye in the extended region.

The shape change can be implemented in different embodiments by different methods. For example, in systems where the contact lens 220 is formed from a flexible or deformable material, the shape of the contact lens 220 can be changed by increasing the pressure exerted by the lens support system 210. The pressure can be increased by increasing suction applied to the adjustable coupler 230 through the vacuum hose 232. In other embodiments, the pressure can be increased by the surgeon manually lowering the lens support system 210 towards the eye 1 after the adjustable coupler 230 has been coupled to the eye by the suction ring 231.

In yet other embodiments, the ophthalmic surgical laser system 100 can include the actuator 240, coupled to the lens support system 210, the adjustable coupler 230, the contact lens 220, or to a combination of these. The actuator 240 can include a mechanical, a friction-based, a spring-loaded, an adhesive-based, a pneumatic, a chemical, a thermal, a magnetic, an electric, or an electromagnetic system. The actuator 240 can be energized by a motor, a piezo-electric system, an electronic control system, or an electromagnetic system. The actuator 240 can actuate the adjustable coupler 230 to enable the change between the central applanation and the extended applanation by changing the shape of the contact lens 220.

In some embodiments, the contact lens 220 can include a rheological fluid, and the actuator 240 can vary a flexibility of the contact lens 220 by applying a magnetic field.

In some embodiments, the actuator 240 may be able to lower the lens support system 210 towards the eye, resulting in a variation of the shape of the contact lens 220.

Figure 8A:
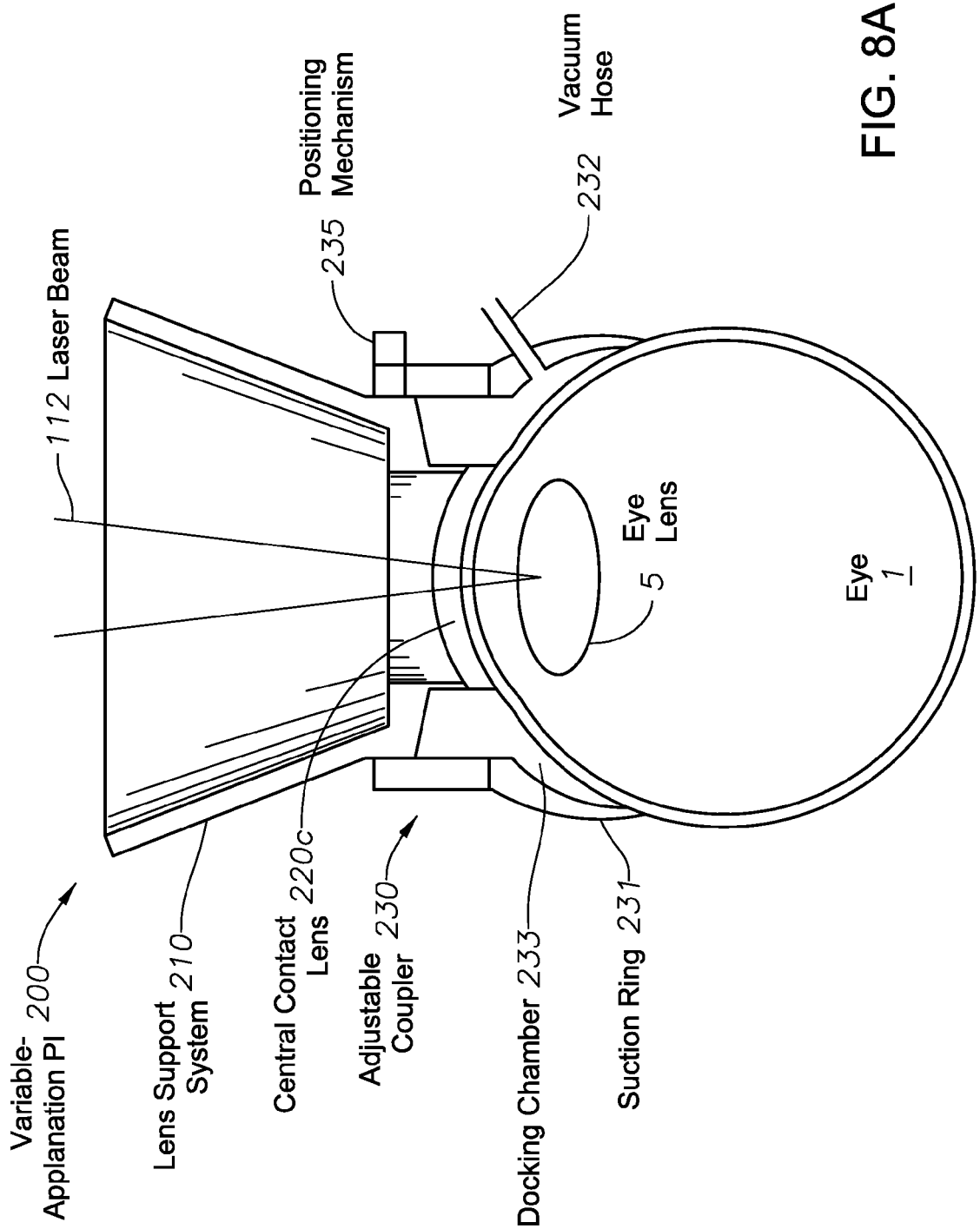
FIGS. 8A-D illustrate an embodiment of a variable applanation patient interface.
Figure 8B:
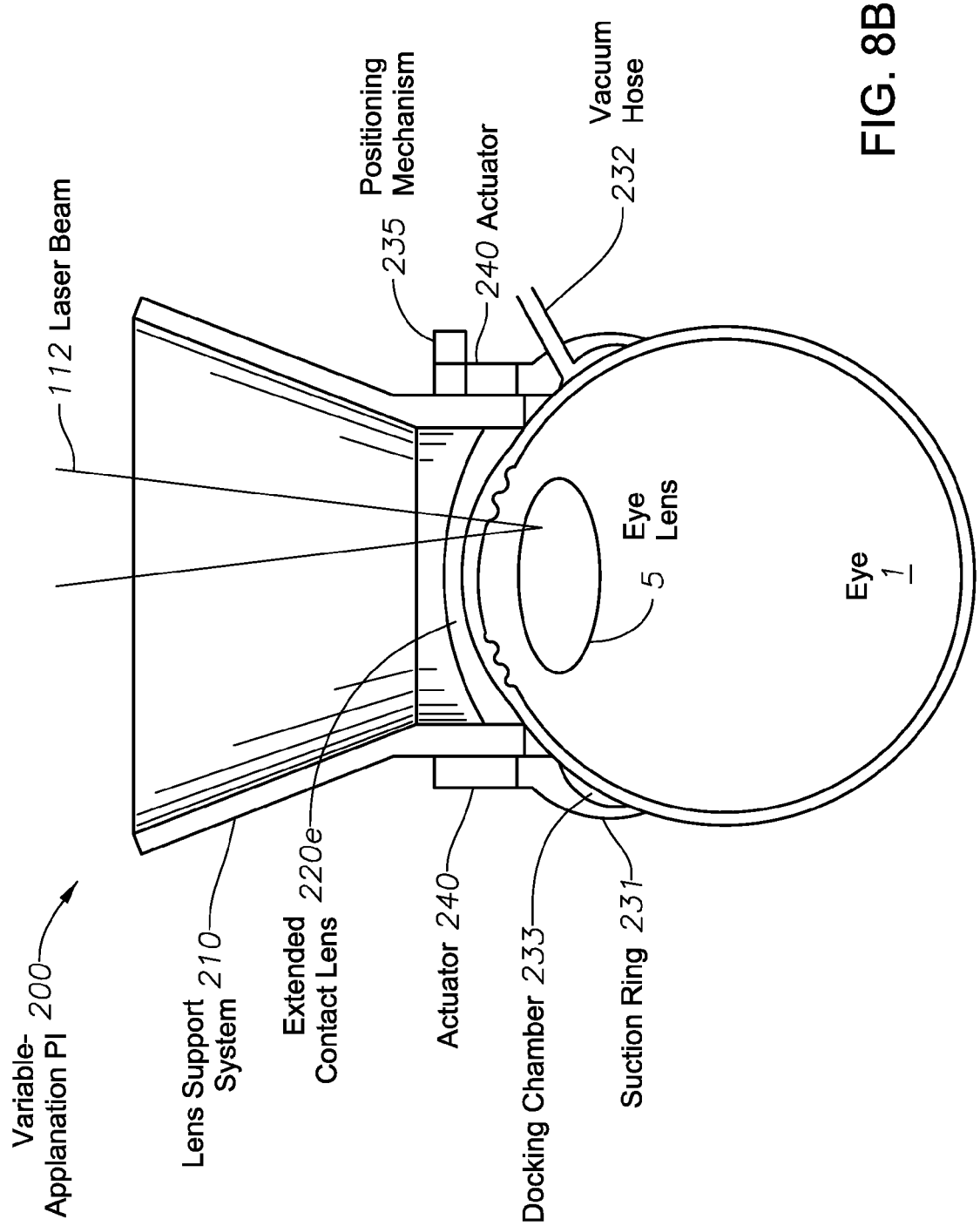

FIGS. 8A-B illustrate an embodiment of the VA-PI 200 that can include a lens support system 210, attachable to the distal end of the ophthalmic surgical laser system 100. This embodiment of the VA-PI 200 can vary the applanation by exchanging the contact lens 220 itself. The lens support system 210 can support a central contact lens 220c that can contact a central region of an eye-surface with a central applanation. The lens support system 210 can also enable the exchange of the central contact lens 220c to an extended contact lens 220e and support the extended contact lens 220e to contact an extended region of the eye-surface, larger than the central region, with an extended applanation.

In addition, the VA-PI 200 can include the adjustable coupler 230 that can be coupled to at least one of the lens support system 210, the central contact lens 220c and the extended contact lens 220e, where the adjustable coupler 230 can be coupled to a non-central region of the eye-surface.

Figure 8C:
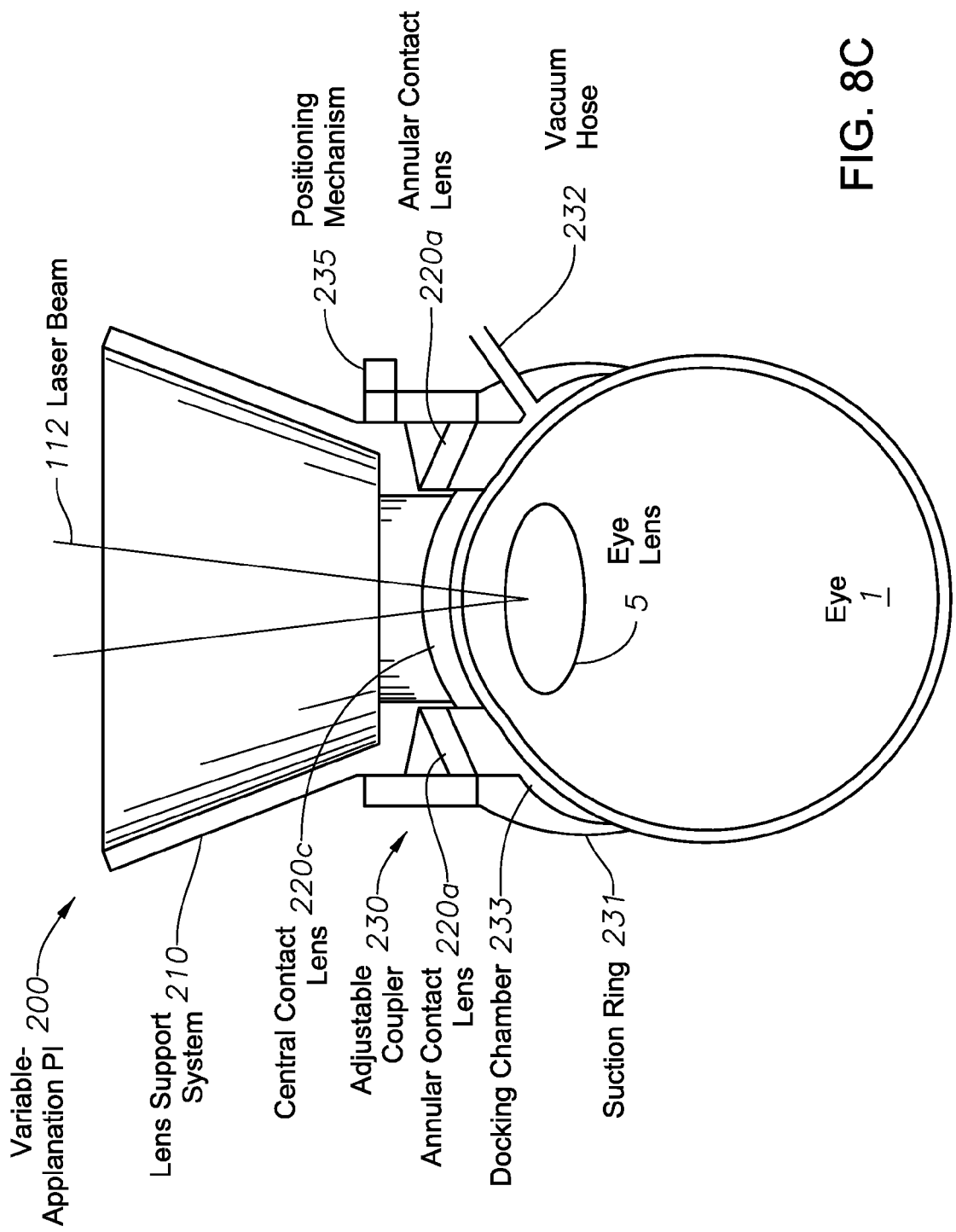
Figure 8D:
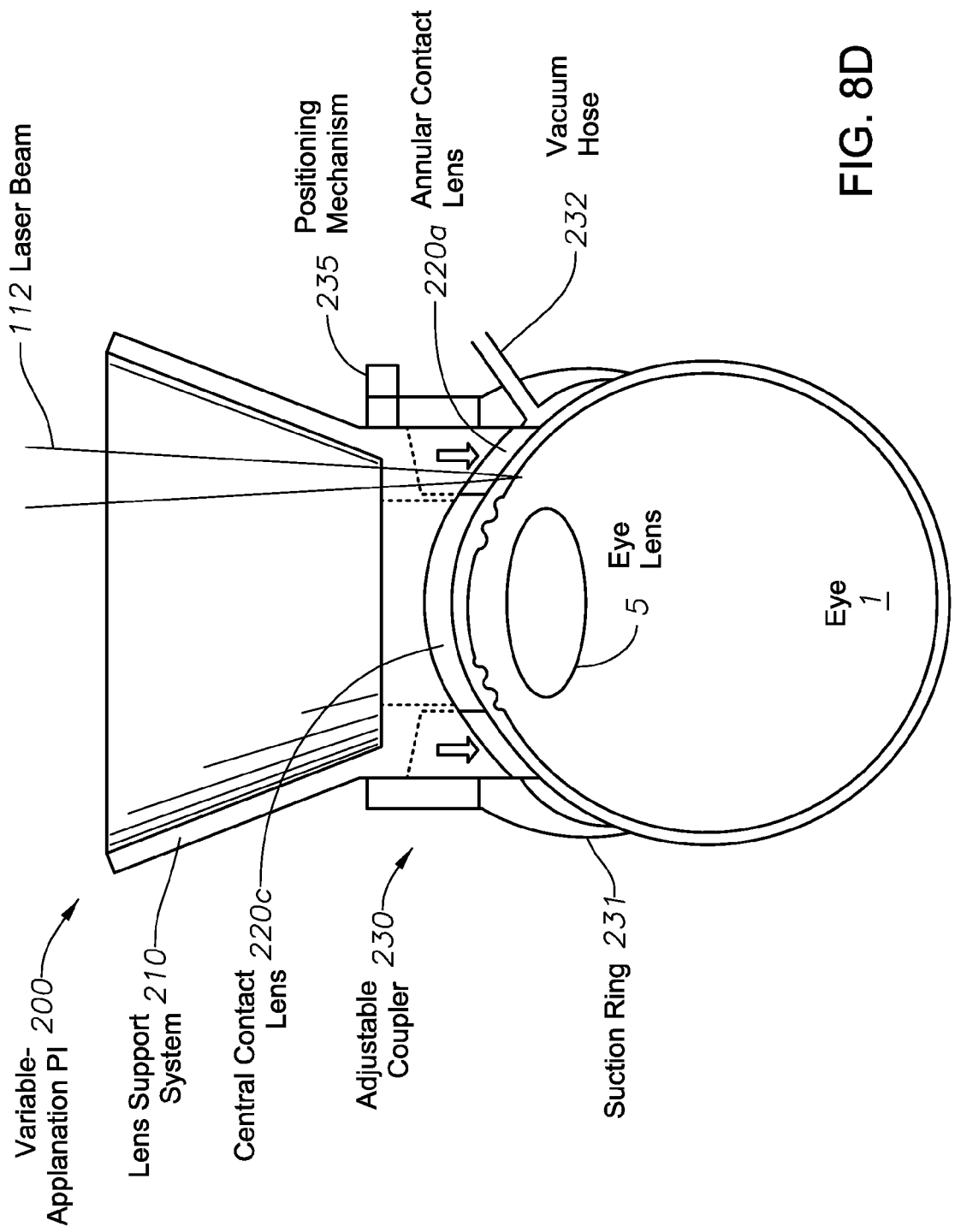

FIGS. 8C-D illustrate that in some segmented-lens embodiments of the VA-PI 200 the extended contact lens 220e can include an annular contact lens 220a, attachable to the lens support system 210 without the removal of the central contact lens 220c. The annular contact lens 220a can be lowered onto the eye-surface when the cataract surgery proceeds from a first, central stage to a second, peripheral or corneal stage. Or, equivalently, the annular contact lens 220a can be raised from the eye-surface when the cataract surgery proceeds from a first, corneal stage to a second, central stage.

Figure 9:
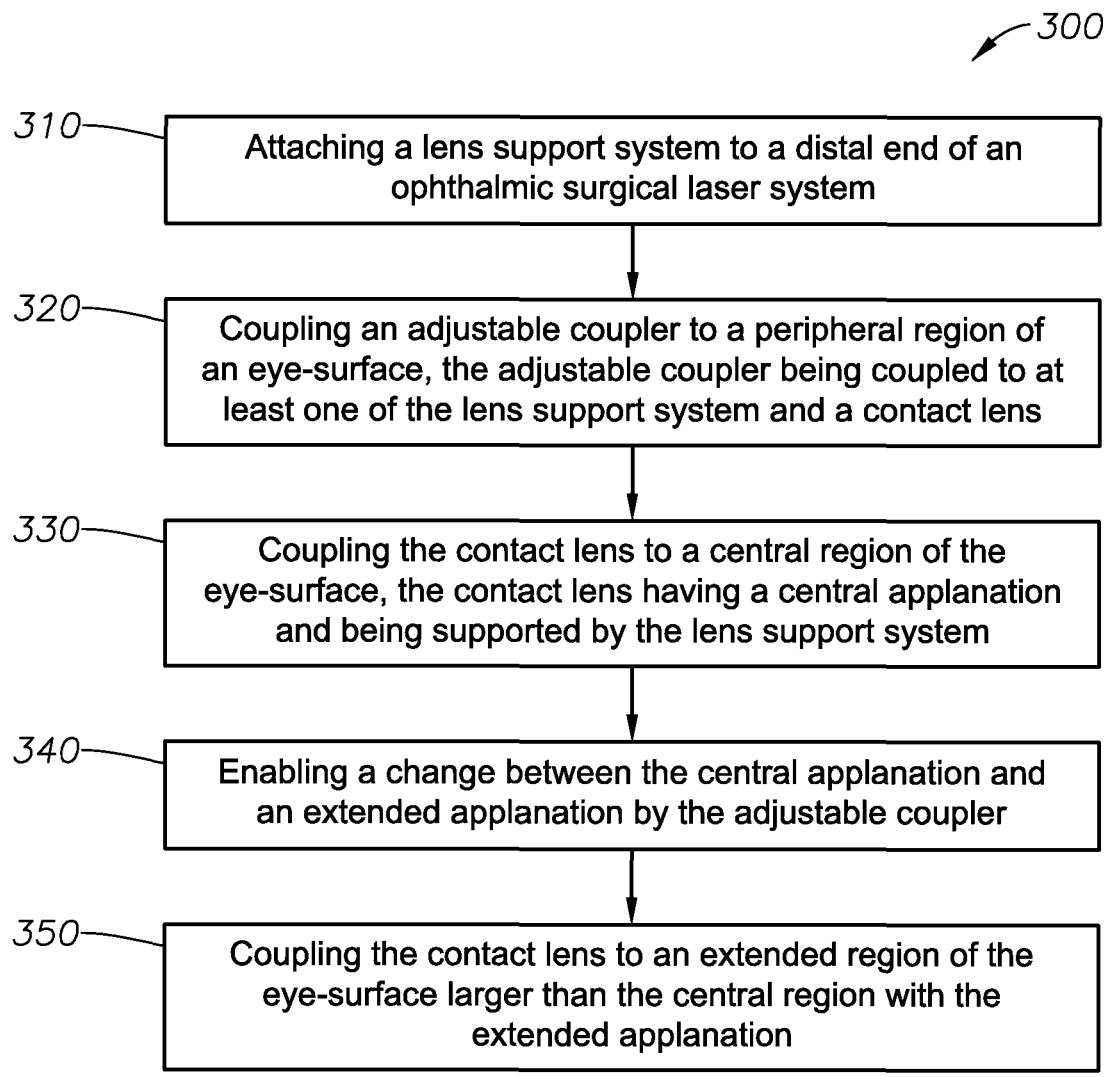
FIG. 9 illustrates a method of ophthalmic surgery.

FIG. 9 illustrates that a method of ophthalmic surgery 300 can include an attaching 310 of a lens support system to a distal end of an ophthalmic surgical laser system; a coupling of an adjustable coupler 320 to a peripheral region of an eye-surface, the adjustable coupler being coupled to at least one of the lens support system and a contact lens; a coupling of the contact lens to a central region 330 of the eye-surface, the contact lens having a central applanation and being supported by the lens support system; an enabling 340 a change between the central applanation and an extended applanation by the adjustable coupler; and a coupling of the contact lens to an extended region 350 of the eye-surface larger than the central region with the extended applanation.

The method 300 can reduce the deformation and wrinkling of the corneal tissue for the central stage of cataract surgeries involving the photodisruption of the lens and the capsulotomy, thus avoiding the energy density dropping below the plasma threshold, the laser beam getting misdirected and the lens getting shifted or rotated. For all these reasons, using the method 300 can increase the precision and efficiency of cataract surgeries.

Here, the ophthalmic surgical laser system can be the above ophthalmic surgical laser system 100, the lens support system can be the above lens support system 210, the contact lens the above contact lens 220, and the adjustable coupler the above adjustable coupler 230.

The enabling 340 can include enabling the change between the central applanation and the extended applanation without releasing the coupling of the adjustable coupler to the peripheral region of the eye-surface. The enabling 340 can also include enabling the changing of the applanation as part of an ophthalmic procedure performed with the ophthalmic surgical laser system.

In some embodiments of the method 300, the coupling the contact lens to the central region 330 of the eye-surface can include enabling the ophthalmic surgical laser system to perform a cataract laser procedure, a capsulotomy, a lens lysis, a photodisruption, or a lens chop of a lens of the eye; and the coupling the contact lens to the extended region 350 of the eye-surface can include enabling the ophthalmic surgical laser system to form a limbal relaxing incision, an arcuate incision, an anterior chamber access cut, an anterior chamber entry cut, a flap-cut or a corneal refractive procedure.

In some embodiments of the method 300, the enabling 340 can include varying at least one of a position and a shape of the contact lens 220 by the adjustable coupler 230.

In some embodiments of the method 300 the sequence of the steps can be reversed: the enabling 340 can include enabling a change from the central applanation to the extended applanation, or enabling a change from the extended applanation to the central applanation.

Figure 10:
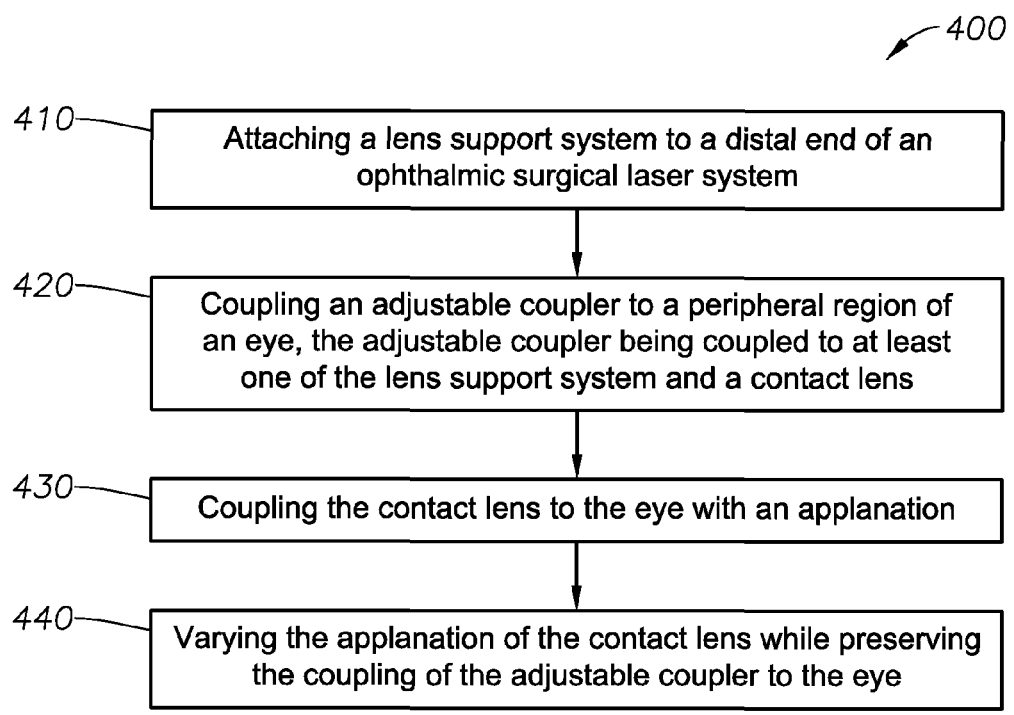
FIG. 10 illustrates a method of ophthalmic surgery.

FIG. 10 illustrates that a method of ophthalmic surgery 400 can include an attaching 410 of a lens support system to a distal end of an ophthalmic surgical laser system; a coupling of an adjustable coupler 420 to a peripheral region of an eye, the adjustable coupler being coupled to at least one of the lens support system and a contact lens; a coupling of the contact lens 430 to the eye with an applanation; and a varying 440 of the applanation of the contact lens while preserving the coupling of the adjustable coupler to the eye. As discussed before, systems that allow a release of this coupling require the reestablishment of the coupling that can be time consuming and imprecise, possibly endangering the efficacy of the ophthalmic cataract surgery.

In some embodiments, the coupling of the adjustable coupler 420 can include coupling the adjustable coupler to the peripheral region of the eye by applying suction to a suction ring of the adjustable coupler; and the varying 440 can include changing the suction.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

What is claimed is:

1. A variable-applanation patient interface, comprising:
   a lens support system, attachable to a distal end of an ophthalmic surgical laser system;
   a contact lens, supported by the lens support system, configured to make contact with an eye-surface; and
   an adjustable coupler, coupled to at least one of the lens support system and the contact lens, and configured
      to be coupled to a non-central region of the eye-surface,
      to accommodate the contact lens to contact a central region of the eye-surface with a central applanation,
      to accommodate the contact lens to contact an extended region of the eye-surface larger than the central region with an extended applanation, and
      to enable a change between the central applanation and the extended applanation by changing a configuration of the adjustable coupler relative to the lens support system.

2. The variable-applanation patient interface of claim 1, wherein:

the adjustable coupler is configured to enable the change between the central applanation and the extended applanation of the contact lens without releasing the coupling to the non-central region of the eye-surface.

3. The variable-applanation patient interface of claim 1, wherein the adjustable coupler being configured to enable a change between the central applanation and the extended applanation comprises:
the adjustable coupler being configured to enable at least one of
a change from the central applanation to the extended applanation, and
a change from the extended applanation to the central applanation.

4. The variable-applanation patient interface of claim 1, wherein:
the adjustable coupler is integrated with the lens support system.

5. The variable-applanation patient interface of claim 1, the adjustable coupler comprising:
a suction ring, configured to form an airtight contact with the eye-surface; and
a vacuum hose, to connect a suction pump with a docking chamber, formed by the contact lens, the suction ring, and the eye-surface, wherein
the suction ring comprises at least one of a ring, a skirt, a cone, and an airtight structure.

6. The variable-applanation patient interface of claim 1, wherein:
the contact lens making contact with the central region of the eye-surface enables the ophthalmic surgical laser system to perform at least one of
a cataract laser procedure, a capsulotomy, a lens lysis, a photodisruption, and a lens chop of a lens of the eye; and
the contact lens making contact with the extended region of the eye-surface enables the ophthalmic surgical laser system to form at least one of
a limbal relaxing incision, an arcuate incision, an anterior chamber access cut, an anterior chamber entry cut, a flap-cut and a corneal refractive procedure.

7. The variable-applanation patient interface of claim 1, wherein:
a radius of the central region is in the range of 2-5 mm; and
a radius of the extended region is in the range of 4-9 mm.

8. The variable-applanation patient interface of claim 1, wherein:
the adjustable coupler being configured to accommodate the contact lens with the central applanation comprises the adjustable coupler being configured to position the contact lens in a first lens position;
the adjustable coupler being configured to accommodate the contact lens with the extended applanation comprises the adjustable coupler being configured to position the contact lens in a second lens position, and
the adjustable coupler being configured to enable a change between the central applanation and the extended applanation comprises the adjustable coupler being configured to enable a repositioning of the contact lens between the first lens position and the second lens position.

9. The variable-applanation interface of claim 8, wherein:
the ophthalmic surgical laser system comprises
an actuator, coupled to at least one of the lens support system, the contact lens and the adjustable coupler, and comprising at least one of a mechanical, a friction-based, a spring-loaded, an adhesive-based, a pneumatic, a chemical, a thermal, a magnetic, an electric and an electromagnetic system, wherein
the actuator is configured to actuate the adjustable coupler to enable the change between the central applanation and the extended applanation by repositioning the contact lens.

10. The variable-applanation patient interface of claim 8, comprising:
a flexible connector, configured
to connect the adjustable coupler to the lens support system,
to assume a first connector configuration to position the contact lens in the first lens position,
to assume a second connector configuration to position the contact lens in the second lens position, and
to be able to change configuration between the first connector configuration and the second connector configuration.

11. The variable-applanation patient interface of claim 8, wherein:
the lens support system and the adjustable coupler are separable elements; and
the variable-applanation patient interface comprises a positioning mechanism that is configured
to accommodate the lens support system and the adjustable coupler to assume a first relative position to position the contact lens in the first lens position,
to accommodate the lens support system and the adjustable coupler to assume a second relative position to position the contact lens in the second lens position, and
to enable the lens support system and the adjustable coupler to change between the first relative position and the second relative position.

12. The variable-applanation patient interface of claim 11, wherein:
the adjustable coupler comprises a hollow cylinder that can be mated slideably to a hollow cylinder of the lens support system; and
the positioning mechanism is configured to lock the cylinder of the lens support system to the cylinder of the adjustable coupler.

13. The variable-applanation patient interface of claim 1, wherein:
the adjustable coupler comprises
an inner suction ring, defining an inner docking chamber coupled to an inner vacuum hose, and
an outer suction ring, defining an outer docking chamber, coupled to an outer vacuum hose, wherein
the inner and outer vacuum hoses are capable of coupling the corresponding inner and outer docking chambers to one or more vacuum pumps.

14. The variable-applanation patient interface of claim 13, wherein:
the variable-applanation patient interface is configured to enable the contact lens to make contact with the central region of the eye-surface when a first suction is applied to the outer docking chamber through the outer vacuum hose; and
the variable-applanation patient interface is configured to enable the contact lens to make contact with the extended region of the eye-surface when a second suction is applied to the inner docking chamber through the inner vacuum hose.

15. The variable-applanation patient interface of claim 1, wherein:

the adjustable coupler being configured to accommodate the contact lens with the central applanation comprises the adjustable coupler being configured to accommodate a shape of the contact lens to assume a first lens shape;

the adjustable coupler being configured to accommodate the contact lens with the extended applanation comprises the adjustable coupler being configured to accommodate the shape of the contact lens to assume a second lens shape; and the adjustable coupler being configured to enable a change between the central applanation and the extended applanation comprises the adjustable coupler being configured to enable the shape of the contact lens to change between the first lens shape and the second lens shape.

16. The variable-applanation interface of claim 15, wherein:

the ophthalmic surgical laser system comprises
an actuator, coupled to at least one of the lens support system, the contact lens and the adjustable coupler, and comprising at least one of a mechanical, a friction-based, a spring-loaded, an adhesive-based, a pneumatic, a chemical, a thermal, a magnetic, an electric, and an electromagnetic system, wherein
the actuator is configured to actuate the adjustable coupler to enable the change between the central applanation and the extended applanation by changing the shape of the contact lens.

17. The variable-applanation patient interface of claim 16, wherein:

the actuator comprises a suction pump, configured to vary the shape of the contact lens by increasing a suction applied to the adjustable coupler, wherein the contact lens comprises a material capable of changing its shape.

18. The variable-applanation patient interface of claim 16, wherein:

the contact lens comprises a rheological fluid, and the actuator is configured to vary a flexibility of the contact lens by applying a magnetic field.

19. The variable-applanation patient interface of claim 16, comprising:

the actuator is configured to lower the lens support system towards the eye, resulting in a variation of the shape of the contact lens.

\* \* \* \* \*